United States Patent [19]

Kume et al.

[11] Patent Number: 5,007,952
[45] Date of Patent: Apr. 16, 1991

[54] HERBICIDAL NOVEL BENZOTHIAZOLONYL PYRROLES

[75] Inventors: Toyohiko Kume; Toshio Goto; Atsumi Kamochi; Akihiko Yanagi; Hiroshi Miyauchi; Tadao Asami, all of Tokyo, Japan

[73] Assignee: Nihon Tokushu Noyaku Seizo K. K., Tokyo, Japan

[21] Appl. No.: 435,223

[22] Filed: Nov. 9, 1989

[30] Foreign Application Priority Data

Nov. 17, 1988 [JP] Japan ................. 63-288796

[51] Int. Cl.$^5$ ............... A01N 43/76; A01N 43/78; A01N 43/86
[52] U.S. Cl. .......................... 71/73; 71/90; 544/58.2; 544/92; 544/135; 544/368; 544/405; 546/198; 546/270; 548/110; 548/125; 548/128; 548/131; 548/134; 548/159; 548/165; 548/170; 548/173; 548/221; 548/172
[58] Field of Search ................ 71/73, 90; 544/135, 544/368, 405; 546/198, 270; 548/110, 125, 128, 131, 134, 159, 165, 170, 173, 172

[56] References Cited

U.S. PATENT DOCUMENTS 4,902,335 2/1990 Kume et al. ................ 548/125

FOREIGN PATENT DOCUMENTS 0170191 5/1986 European Pat. Off. .
0218972 4/1987 European Pat. Off. .
0255601 2/1988 European Pat. Off. .
3809842 10/1989 Fed. Rep. of Germany ...... 546/198

OTHER PUBLICATIONS

Tetrahedron, vol. 23, No. 11, pp. 4469-4479, 1967.
J. Chem. Soc., 1970, No. 18, pp. 2563-2567.
J. Heterocycl. Chem., vol. 9, No. 6, pp. 1413-1417, 1972.
Khim. Farm. Zh., vol. 10, No. 9, pp. 55-60, 1976.
Chem. Soc. of Japan, vol. 41, pp. 2849-2852, 1968.

Primary Examiner—Mukund J. Shah
Assistant Examiner—Philip Datlow
Attorney, Agent, or Firm—Sprung Horn Kramer & Woods

[57] ABSTRACT

Herbicidally active pyrroles of the formula

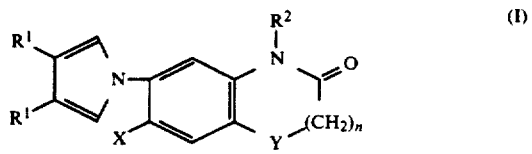

wherein $R^1$ represents $C_{1-4}$ alkyl, or one $R^1$ together with the other $R^1$ forms tetramethylene or butenylene,
X represents hydrogen or halogen,
Y represents O or S,
n represents 0 or 1,
$R^2$ represents hydrogen or an organic radical.

8 Claims, No Drawings

HERBICIDAL NOVEL BENZOTHIAZOLONYL PYRROLES

The present invention relates to novel pyrroles, to processes for their preparation and to their use as herbicides.

A certain kind of 1-arylpyrroles has already been disclosed in Tetrahedron vol. 23, No. 11, pp. 4469–4479, 1967, J. Chem. Soc., 1970, No. 18, pp. 2563–2567, J. Heterocycl. Chem. vol. 9, No. 6, pp. 1413–1417, 1972 and Khim. Farm. Zh., vol. 10, No. 9, pp. 55–60, 1976, but no disclosure is of herbicidal activities therein.

There have been found novel pyrroles of the formula (I)

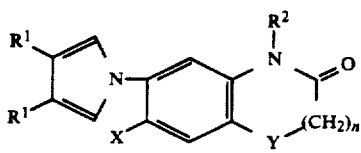

wherein
$R^1$ represents $C_{1-4}$ alkyl, or one $R^1$ may form, together with another $R^1$, tetramethylene or butenylene,
X represents hydrogen or halogen,
Y represents O or S,
n represents 0 or 1,
$R^2$ represents hydrogen, $C_{1-5}$ alkyl, halogeno-$C_{1-5}$ alkyl, cyclopropylmethyl, $C_{3-4}$ alkenyl, halogeno-$C_{3-4}$ alkenyl, $C_{3-4}$ alkynyl, $C_{1-3}$ alkoxy-$C_{1-2}$ alkyl, $C_{1-3}$ alkylthio-$C_{1-2}$ alkyl, $C_{1-3}$ alkylsulfinyl-$C_{1-2}$ alkyl, $C_{1-3}$ alkylsulfonyl-$C_{1-2}$ alkyl, phenylthio-$C_{1-2}$ alkyl optionally substituted by halogen; phenylsulfinyl-$C_{1-2}$ alkyl, phenylsulfonyl-$C_{1-2}$ alkyl, cyano-$C_{1-2}$ alkyl, carbamoylmethyl, thiocarbamoylmethyl, tri-$C_{1-3}$ alkylsilylmethyl, phenyl-$C_{1-2}$ alkyl optionally substituted by halogen, methyl or methoxy; or $R^2$ furthermore represents

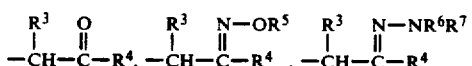

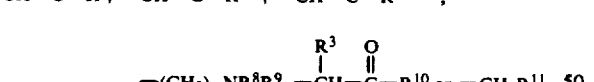

wherein
m represents 2 or 3,
$R^3$ represents hydrogen or $C_{1-4}$ alkyl,
$R^4$ represents $C_{1-4}$ alkyl, or phenyl optionally substituted by halogen or $C_{1-4}$ alkyl,
$R^5$ represents hydrogen, $C_{1-4}$ alkyl, $C_{3-4}$ alkenyl, $C_{3-4}$ alkynyl, benzyl, $C_{1-4}$-alkyl-carbonyl, or $C_{1-4}$ alkanesulfonyl,
$R^6$ and $R^7$ each represent $C_{1-4}$ alkyl or $C_{1-4}$ alkylcarbonyl,
$R^8$ represents $C_{1-5}$ alkyl,
$R^9$ represents $C_{1-5}$ alkyl or $C_{1-4}$ alkyl-carbonyl or $R^8$ and $R^9$ may form a 5–6 membered heterocyclic ring together with the nitrogen atom, to which they are bonded, while said heterocyclic ring may comprise.

or O as a ring forming member,
$R^{10}$ represents $C_{1-6}$ alkoxy, $C_{3-7}$ cycloalkoxy, $C_{2-3}$ haloalkoxy, $C_{1-5}$ alkylamino, $C_{2-8}$ dialkylamino, or N-$C_{1-4}$ alkyl-N-phenylamino wherein the phenyl of the N-phenyl may be substituted by halogen and/or methyl or $R^{10}$ represents N,N-$C_{4-6}$ polymethyleneamino or tri-$C_{1-3}$ alkylsilylmethoxy, and
$R^{11}$ represents a 5–6 membered heterocyclic group comprising at least one nitrogen agom and being optionally substituted by $C_{1-4}$ alkyl or $C_{1-4}$ alkoxy.

In case of substituted radicals the substitution may be identically or differently, mono- or polysubstituted, preferably mono- to pentasubstituted, in particular mono-, di- or trisubstituted.

The pyrroles of the formula (I) can be prepared when
(a) compounds of the formula (II)

wherein $R^1$ represents the same radicals as mentioned above,
are reacted with compounds of the formula (III)

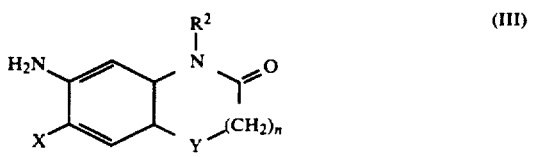

wherein X, Y, n and $R^2$ represent the same radicals as mentioned respectively above,
in the presence of inert solvents, or (b) [where $R^2$ represents other radicals than a hydrogen atom, $R^2$ is replaced by $R^{2-1}$] compounds of the formula (IV)

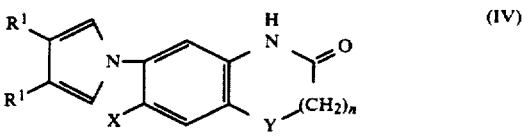

wherein $R^1$, X, Y and n represent the same radicals as mentioned respectively above,
are reacted with compounds of the formula (V)

wherein $R^{2-1}$ represents the same radicals mentioned above, and M represents a halogen atom, methansulfonyloxy, tosyloxy or $R^{2-1}$—OSO$_2$—O— with $R^{2-1}$ denoting the same as mentioned above,
in the presence of inert solvents and if appropriate, in the presence of a base.

The pyrroles represented by the formula (I) according to the present invention exhibit strong herbicidal activities, in particular against upland-weeds, and exhibit good compatibility with crops.

Among the pyrroles according to the invention, of the formula (I), preferred compounds are those in which $R^1$ represents $C_{1-4}$ alkyl, or one $R^1$ may form, together with another $R^1$, tetramethylene or butenylene, X represents hydogen, chlorine or fluorine,
Y represents O or S,
n represents 0 or 1,
$R^2$ represents hydrogen, $C_{1-3}$ alkyl, cyclopropylmethyl,
$C_3$ alkenyl optionally substituted by chlorine; propargyl, $C_{1-2}$ alkoxy-$C_{1-2}$-alkyl, $C_{1-2}$ alkylthio-$C_{1-2}$ alkyl, $C_{1-2}$ alkylsulfinyl-$C_{1-2}$ alkyl, $C_{1-2}$ alkylsulfonyl-$C_{1-2}$ alkyl, phenylthiomethyl optionally substituted by chlorine; phenylsulfinylmethyl, phenylsulfonylmethyl, cyanomethyl, carbamoylmethyl, thiocarbamoylmethyl, trimethylsilylmethyl, benzyl optionally substituted by fluorine, chlorine, methyl or methoxy, or $R^2$ furthermore represents $$\begin{array}{ccc} R^3 & O & R^3 & N-OR^5 & R^3 & N-NR^6R^7 \\ | & \| & | & \| & | & \| \\ -CH-C-R^4, & -CH-C-R^4, & -CH-C-R^4, \end{array}$$

$$\begin{array}{cc} R^3 & O \\ | & \| \\ -(CH_2)_m NR^8R^9, & -CH-C-R^{10} \text{ or } -CH_2R^{11}, \end{array}$$

in which
m represents 2 or 3,
$R^3$ represents hydrogen, methyl or ethyl,
$R^4$ represents methyl, ethyl, propyl or isopropyl, or phenyl which is optionally substituted by chlorine or methyl,
$R^5$ represents hydrogen, methyl, ethyl, propyl, isopropyl, allyl, propargyl, benzyl, acetyl or methanesulfonyl,
$R^6$ and $R^7$ represent methyl, ethyl or acetyl,
$R^8$ represents $C_{1-4}$ alkyl, $R^9$ represents $C_{1-4}$ alkyl, acetyl or methanesulfonyl or $R^8$ and $R^9$ may form, together with the adjoining nitrogen atom, pyrrolidine, piperidine, N-methylpiperazine, piperazine or morpholine,
$R^{10}$ represents $C_{1-4}$ alkoxy, $C_{3-6}$ cycloalkoxy, $C_{2-3}$ fluoroalkoxy, $C_{1-4}$ alkylamino, $C_{2-6}$ dialkylamino, N-$C_{1-3}$ alkyl-N-phenylamino wherein the phenyl of the N-phenyl may be substituted by chlorine and/or methyl, or $R^{10}$ represents piperidino or trimethylsilymethoxy, and
$R^{11}$ represents a 5-membered heterocyclic group comprising one or two nitrogen atoms and optionally one oxygen atom, sulfur atom,
which may optionally be substituted by methyl, methoxy or ethoxy or $R^{11}$ represents a six-membered heterocyclic group comprising one or two nitrogen atoms.

Very particularly preferred pyrroles of the formula (I) are those in which
$R^1$ represents methyl or one $R^1$ may form, together with another $R^1$, tetramethylene or butenylene.
X represents fluorine,
Y represents O or S,
n represents 0 or 1,
$R^2$ represents hydrogen, methyl, ethyl, n- or i-propyl, cyclopropylmethyl, allyl optionally substituted by chlorine; methoxymethyl, ethoxymethyl, methylthiomethyl, ethylthiomethyl, methylsulfinylmethyl, methylsulfonylmethyl, 2-oxopropyl, methoxycarbonylmethyl, ethoxycarbonylmethyl or $-CH_2R^{11}$, in which $R^{11}$ represents a 5-membered heterocyclic group comprising one or two nitrogen atoms and furthermore optionally one oxygen atom, sulfur atom or nitrogen atom, which may optionally be substituted by methyl; or a six-membered heterocyclic group comprising one or two nitrogen atoms.

Regarding the above-mentioned definitions of $R^{11}$, the specific examples of the five- or six-membered heterocyclic ring include thiazole, isoxazole, 1,2,4-thiazole, 1,2,4-oxadiazole, 1,2,5-oxadiazole, 1,2,5-thiadiazole, pyridine, pyrazine and so on.

Specifically, the following compounds may be mentioned:
2-[7-fluoro-2H-1,4-benzoxazin-3(4H)-on-6-yl]-4,5,6,7-tetrahydroisobenzindole,
2-[7-fluoro-4-propargyl-2H-1,4-benzoxazin-3(4H)-on-6-yl]-4,5,6,7-tetrahydroisobenzindole,
2-(6-fluoro-2-benzothiazolon-5-yl)-4,5,6,7-tetrahydroisobenzindole, and
2-(6-fluoro-3-propargyl-2-benzothiazolon-5-yl)-4,5,6,7-tetrahydroisobenzindole.

If as starting materials in the above-mentioned process (a) are employed, for instance, 1,2-cyclohexanedicarboxyaldehyde and 6-amino-7-fluoro-2H-1,4 benzoxazin -3(4H)-one, the reaction can be expressed by the following scheme:

If as starting materials in the above-mentioned process (b) are employed, for example, 2-[7-fluoro-2H-1,4-benzoxazin-3(4H)-on-6-yl]-4,5,6,7-tetrahydroisobenzoindole and propargyl bromide, the reaction can be expressed by the following scheme:

Regarding the compounds of the formula (II) employed as starting materials in the process (a), $R^1$ in this formula has the same meaning as stated before. Furthermore, in the formula (II), $R^1$ preferably has the same preferred meaning as stated before.

The compounds of the formula (II) are known in themselves, and 1,2-cyclohexanedicarboxyaldehyde, among others, can generally be prepared according to the process disclosed by Ann. vol. 560, page 1, 1984 wherein cyclooctatetrane is guided to 7,8-dihydroxybicyclo[4,2,0]-octane through a four-stage reaction, which is then reacted with lead tetracetate at the final reaction stage.

Further, the compounds of the formula (II) mentioned above can be prepared by the process that was disclosed by J. Am. Chem. Soc., Div. Polymer Chem, Preprints, vol. 5, No. 1, pages 210–215, 1964, wherein 1,2-cyclohexanedicarboxylic acid is converted to the corresponding dicarboxylic acid chloride that is in turn reacted with N-methyl aniline to form the corresponding bis-(N-methylanilide) which is then reduced with lithium aluminum hydride, or according to the process disclosed by J. Am. Chem. Soc., vol. 74, pages 3014–3018, 1952, wherein 4-cyclohexane-1,2-dicarboxyaldehyde is formed from 2,5-dimethoxy-2,5-dihydrofuran and butadiene, which is then catalytically reduced.

In addition, besides the above-mentioned three known processes, 1,2-cyclohexanedicarboxyaldehyde can be obtained by a process in which (c) 1,2-cyclohexanedimethanol having the following formula:

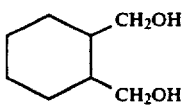

is oxidized.

The above-mentioned 1,2-cyclohexanedimethanol can be easily obtained by reducing 1,2-cyclohexanedicarboxylic anhydride, according to a known process.

As the oxidizing agent employed in the process (c), use may be made, for example, of dimethylsulfoxide-oxalic dichloride (J. Org. Chem. vol. 44, page 4148, 1979), pyridinium dichromate (Tetr. Letter, page 399, 1979), pyridinium chlorochromate (Tetr. Letter, page 2647, 1975), manganese dioxide, oxygen, lead tetraacetate, copper oxide, ammonium cerium (IV) nitrate (Synthesis, page 347, 1973), palladium (II) salt, dimethylsulfoxide-dicyclohexylcarbodiimide (J. Am. Chem. Soc. vol. 85, page 3027, 1963) and so on.

As compared with any known process, the above-mentioned process (c) requires the minimum number of steps as well as very simple procedures.

Regarding the compounds of the formula (III) employed in the process (a), the compounds are those as defined under the above-mentioned X, Y, n and $R^2$.

In the formula (III), X, Y, n and $R^2$ have the same preferred meanings as mentioned before.

The compounds of the formula (III) include known compounds which can be easily prepared by the processes disclosed by Japanese Patent Application No. 258462/1987.

Examples of the compounds of the formula (III) include:
6-amino-7-fluoro-2H-1,4-benzoxazin-3(4H)-one,
6-amino-7-fluoro-4-propyl-2H-1,4-benzoxazin-3(4H)-one,
6-amino-7-fluoro-4-propargyl-2H-1,4-benzoxazin-3(4H)-one,
6-amino-7-fluoro-4-(pyridine-2-ylmethyl)-2H-1,4-benzoxazin-3(4H)-one,
6-amino-7-fluoro-4-(isoxazol-3-ylmethyl)-2H-1,4-benzoxazin-3(4H)-one,
5-amino-6-fluoro-2-benzothiazolone,
5-amino-6-fluoro-3-propyl-2-benzothiazolone,
5-amino-6-fluoro-3-propenyl-2-benzothiazolone,
5-amino-6-fluoro-3-propargyl-2-benzothiazolone,
5-amino-6-fluoro-3-(isoxazol-3-ylmethyl)-2-benzothiazolone,
5-amino-6-fluoro-3-(pyridin-2-ylmethyl)-2-benzothiazolone,
5-amino-6-fluoro-2-benzoxazolone,
5-amino-6-fluoro-3-propargyl-2-benzoxazolone, and
5-amino-6-fluoro-3-(pyridin-2-ylmethyl)-2-benzoxazolone.

The starting materials of the formula (IV) employed in the process (b) mentioned above are included in the formula (I) and can be easily prepared by the above-mentioned process (a).

For the compounds of the formula (V), $R^{2-1}$ and M have the same meanings as mentioned before and $R^{2-1}$ has the preferable meanings as mentioned regarding $R^2$, excluding the hydrogen atom only, while M represents a chlorine atom, bromine atom, iodine atom, methanesulfonyloxy, tosyloxy or $R^{2-1}$ —$OSO_2$—O—, wherein $R^{2-1}$ has the same preferred meaning as defined for $R^{2-1}$.

The compounds of the formula (V) are well known in the organic chemical field and, as specific examples, include:

methyl iodide, ethyl iodide, n-propyl iodide, isopropyl iodide, cyclopropylmethyl bromide, chloromethyl methyl ether, chloromethyl ethyl ether, chloromethyl methyl sulfide, chloromethyl ethyl sulfide, benzyl chloride, o-fluorobenzyl, chloride, p-fluorobenzyl chloride, o-chlorobenzyl chloride, p-chlorobenzyl chloride, dimethylsulfate, chloro-2-propanone, 3-chloro-2-butanone, 3-bromopropene, 3-bromo-2-methylpropene, 2,3-dichloropropene, 1,3-dichloropropene, 1,2,3-trichloropropene, 1,1,2,3-tetrachloropropene, 3-bromopropyne, 3-bromobutyne, chloroacetonitrile, 2-bromopropionitrile, 2-(chloromethyl)pyridine, 2-(chloromethyl)pyrazine, 1-(chloromethyl)-1H-1,2,4-triazole, 5-(chloromethyl)-1-methyl-1H-1,2,4-triazole, 3-(chloromethyl)isoxazole, 3-(chloromethyl)-5-methyl-1,2,4-oxadiaozole, 5-(chloromethyl)-3-methyl-1,2,4-oxadizole, 3-(bromomethyl)-4-methyl-1,2,5-oxadiazole, 2-(chloromethyl)-5-methyl-1,3,4-oxadiazole, 4-(chloromethyl)thiazole, 3-(chloromethyl)-5-methoxy-1,2,4-thiadiazole, 3-(chloromethyl)-5-ethoxy-1,2,4-thiadiazole, 3-(bromomethyl)-1,2,5-thiadiazole, and 2-(chloromethyl)-5-methyl-1,3,4-thiadiazole, etc.

As appropriate diluents for carrying out the process (a), any kind of inert organic solvents can be mentioned.

As examples of such solvents, use may be made preferably of aliphatic optionally halogenated hydrocarbons such as, for example, petroleum ether, dichloromethane, chloroform, carbon tetrachloride; aromatic optionally halogenated hydrocarbons such as benzene, toluene, xylene, chlorobenzene, and the like; ethers such as, for example, dimethoxyethane, 1,4-dioxane, tetrahydrofuran; alcohols such as methanol, ethanol, ethylcellosolve, ethylene glycol; and organic acids such as acetic acid.

The above-mentioned process (a) may be carried out in the presence of catalysts which can be exemplified by organic acids such as paratoluenesulfonic acid, inorganic acids such as concentrated sulfuric acid, and solid phase acidic catalysts such as ion-exchange resins, silica gel, etc.

The reaction temperature of the process (a) may vary in a fairly wide range. In general, the reaction is carried out at a temperature of about 60° to about 250° C., preferably a temperature of about 100° to about 140° C. It is preferred to carry out the reaction under normal pressure, although a higher or lower pressure can also be used.

In conducting the process (a), about 1 to 1.3 moles of the compounds of the formula (III) may, for instance, be employed per mole of the compound of the formula (II) in the presence of an inert solvent and, as will be stated in the following examples, under refluxing while being heated so that the desired compounds of the formula (I) can be obtained.

In conducting the process (b), use may be made, as appropriate diluents, of inert solvents.

As examples of such solvents, use may be made of water, alcohols such as methanol, ethanol; nitriles such as acetonitrile, propionitrile; ethers such as tetrahydrofuran, 1,4-dioxane; and optionally halogenated hydrocarbons such as petroleum ether, chloroform, carbon tetrachloride, benzene, toluene, xylene and chlorobenzene.

Further, the process (c) may also be carried out in the presence of phase transfer catalysts such as, for example, trimethylbenzyl ammonium chloride, tetrabutylammonium bromide, etc.

The process (b) may be carried out in the presence of a base, for example, selected from the group consisting of sodium carbonate, potassium carbonate, potassium hydroxide, sodium hydroxide, sodium methoxide, sodium ethoxide, potassium tert-butoxide, sodium hydride, etc.

The reaction temperature of the process (b) may vary in a fairly wide range. In general, the reaction is carried out at a temperature of about 20° to about 120° C., preferably a temperature of about 50° to about 90° C.

It is preferred to carry out the reaction under normal pressure, although a higher or lower pressure can also be used.

In conducting the process (b), from 1 to about 1.2 moles of the compounds of the formula (V) may, for instance, be employed per mole of the compounds of the formula (IV) while the reaction is carried out in the presence of a base and inert solvent to obtain the desired compound of the formula (I).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be emplyed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the slective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.0001 and 3 kg of active compound per hectare of soil surface, preferably between 0.001 and 2 kg per ha.

The preparation and use of the active compounds according to the invention can be seen from the following examples.

PREPARATIVE EXAMPLES

EXAMPLE 1

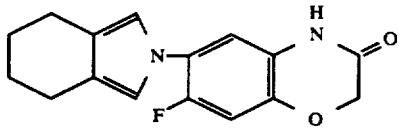

2.8 g of 1,2-cyclohexanedicarboxyaldehyde and 3.64 g of 6-amino-7-fluoro-2H-1,4-benzoxazin-3(4H)-one were added to 100 ml of anhydrous xylene, and then heated under reflux for 30 minutes, while being agitated. After the completion of the reaction, the solvent was distilled off from the reaction solution under a reduced pressure, and the resulting reaction product was recrystallized from acetonitrile to obtain 4.6 g of the desired 2-[7-fluoro-2H-1,4-benzoxazin-3(4H)-on-6-yl]-4,5,6,7-tetrahydroisobenzindole having a melting point in the range from 230° to 234° C.

EXAMPLE 2

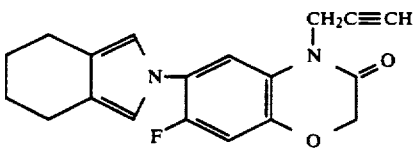

To 30 ml of acetonitrile were added 1.43 g of 2-[7-fluoro-2H-1,4-benzoxazin-3(4H)-on-6-yl]-4,5,6,7-tetrahydroisobenzindole, 0.7 g of propargyl bromide and 1.0 g of potassium carbonate, followed by three-hours boiling under stirring. After the completion of the reaction, the cooled mixture was filtered and the resulting filtrate, after concentration, was purified through silica gel column chromatography (hexane:ethylacetate=9:1) to obtain 1.5 g of the desired crystallized 2-[7-fluoro-4-propargyl-2H-1,4-benzoxazin-3(4H)-on-6-yl]-4,5,6,7-tetrahydroisobenzindole having a melting point in the range from 122° to 130° C.

EXAMPLE 3

(Synthesis of Starting Compounds)

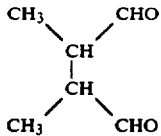

To 20 ml of oxalic chloride under stirring at −70° C. was added dropwise a solution of 34 ml of dimethyl sulfoxide in 100 ml of dichloromethane while the temperature of the reaction solution was kept below −55° C. After the dropwise addition had been completed, the reaction solution was stirred for five minutes and, thereafter, a solution of 11.6 g of 2,3-dimethyl-1,4-butanediol in 100 ml of dichloromethane was added thereto within a five minutes period. After 15 minutes stirring, 140 ml of triethylamine was added to the solution and allowed to stand until it returned to room temperature. The resulting residue was filtered off from the reaction product, the filtrate was concentrated, and the resulting concentrated residue was purified by distillation under reduced pressure. By collecting the resulting fractions boiling in the range from 65° to 68° C. at 3.5 mmHg, 7.5 g of the desired 2,3-dimethyl-1,4-butanedial was obtained.

According to the same procedures as to those employed in the foregoing Examples 1 and 2, the following compounds having the formula (I) of the present invention can be obtained, as shown in Table 1, together with the compounds which were obtained according to the Examples 1 and 2:

TABLE 1

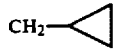

| Comp. No. | $R^1, R^1$ | $R^2$ | X | Y | n | |
|---|---|---|---|---|---|---|
| 1 | $CH_3, CH_3$ | H | F | S | 0 | |
| 2 | $CH_3, CH_3$ | $CH_3$ | F | S | 0 | |
| 3 | $CH_3, CH_3$ | $C_2H_5$ | F | S | 0 | |
| 4 | $CH_3, CH_3$ | $C_3H_7$-n | F | S | 0 | |
| 5 | $CH_3, CH_3$ | $C_4H_9$-n | F | S | 0 | |
| 6 | $CH_3, CH_3$ | $C_4H_9$-iso | F | S | 0 | |
| 7 | $CH_3, CH_3$ | $C_4H_9$-sec | F | S | 0 | |
| 8 | $CH_3, CH_3$ | $CH_2CH_2F$ | F | S | 0 | |
| 9 | $CH_3, CH_3$ | $CH_2CH_2CH_2Cl$ | F | S | 0 | |
| 10 | $CH_3, CH_3$ | $CH_2$-cyclopropyl | F | S | 0 | |
| 11 | $CH_3, CH_3$ | $CH_2CH=CH_2$ | F | S | 0 | |
| 12 | $CH_3, CH_3$ | $CH_2CH_2CH=CH_2$ | F | S | 0 | |
| 13 | $CH_3, CH_3$ | $CH_2C(Cl)=CH_2$ | F | S | 0 | |
| 14 | $CH_3, CH_3$ | $CH_2CH=CHCl$ | F | S | 0 | |
| 15 | $CH_3, CH_3$ | $CH_2C(Cl)=CHCl$ | F | S | 0 | |
| 16 | $CH_3, CH_3$ | $CH_2C(Cl)=CCl_2$ | F | S | 0 | |
| 17 | $CH_3, CH_3$ | $CH_2C\equiv CH$ | H | S | 0 | |
| 18 | $CH_3, CH_3$ | $CH_2C\equiv CH$ | F | S | 0 | mp. 123.5–126.5° C. |
| 19 | $CH_3, CH_3$ | $CH(CH_3)C\equiv CH$ | F | S | 0 | |
| 20 | $CH_3, CH_3$ | $CH_2OCH_3$ | F | S | 0 | |
| 21 | $CH_3, CH_3$ | $CH_2OC_2H_5$ | F | S | 0 | |
| 22 | $CH_3, CH_3$ | $CH_2CH_2OC_2H_5$ | F | S | 0 | |
| 23 | $CH_3, CH_3$ | $CH_2SCH_3$ | F | S | 0 | |
| 24 | $CH_3, CH_3$ | $CH_2SC_2H_5$ | F | S | 0 | |
| 25 | $CH_3, CH_3$ | $CH_2CH_2SC_2H_5$ | F | S | 0 | |
| 26 | $CH_3, CH_3$ | $CH_2S(O)CH_3$ | F | S | 0 | |
| 27 | $CH_3, CH_3$ | $CH_2S(O)_2CH_3$ | F | S | 0 | |
| 28 | $CH_3, CH_3$ | $CH_2S$-phenyl | F | S | 0 | |
| 29 | $CH_3, CH_3$ | $CH_2S$-(4-Cl-phenyl) | F | S | 0 | |

TABLE 1-continued
| 30 | CH₃, CH₃ | 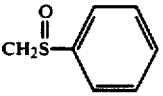 | F | S | 0 |
| 31 | CH₃, CH₃ | 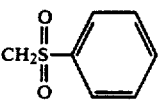 | F | S | 0 |
| 32 | CH₃, CH₃ | CH₂CN | F | S | 0 |
| 33 | CH₃, CH₃ | CH₃–CH–CN | F | S | 0 |
| 34 | CH₃, CH₃ | CH₂CONH₂ | F | S | 0 |
| 35 | CH₃, CH₃ | CH₂CSNH₂ | F | S | 0 |
| 36 | CH₃, CH₃ | CH₂Si(CH₃)₃ | F | S | 0 |
| 37 | CH₃, CH₃ |  | F | S | 0 |
| 38 | CH₃, CH₃ | 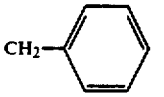 | F | S | 0 |
| 39 | CH₃, CH₃ | 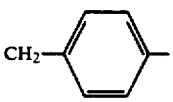 | F | S | 0 |
| 40 | CH₃, CH₃ | 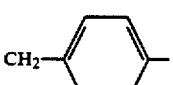 | F | S | 0 |
| 41 | CH₃, CH₃ | 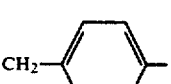 | F | S | 0 |
| 42 | CH₃, CH₃ | CH₂COCH₃ | H | S | 0 |
| 43 | CH₃, CH₃ | CH₂COCH₃ | F | S | 0 |
| 44 | CH₃, CH₃ | CH₂COC₂H₅ | F | S | 0 |
| 45 | CH₃, CH₃ | CH₃–CHCOC₂H₅ | F | S | 0 |
| 46 | CH₃, CH₃ | C₂H₅–CHCOC₃H₇ | F | S | 0 |
| 47 | CH₃, CH₃ | 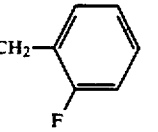 | F | S | 0 |
| 48 | CH₃, CH₃ |  | F | S | 0 |

TABLE 1-continued

| | | | | | |
|---|---|---|---|---|---|
| 49 | CH₃, CH₃ | CH₂—CO—⟨C₆H₄⟩—Cl (4-chlorophenacyl) | F | S | 0 |
| 50 | CH₃, CH₃ | CH₂C(=NOH)—CH₃ | F | S | 0 |
| 51 | CH₃, CH₃ | CH₂C(=NOH)—C₆H₅ | F | S | 0 |
| 52 | CH₃, CH₃ | CH₂C(=NOCH₃)—CH₃ | F | S | 0 |
| 53 | CH₃, CH₃ | CH₂C(=NOCH₃)—C₆H₅ | F | S | 0 |
| 54 | CH₃, CH₃ | CH₂C(=NOC₂H₅)—CH₃ | F | S | 0 |
| 55 | CH₃, CH₃ | CH₂C(=NOCH₂CH=CH₂)—CH₃ | F | S | 0 |
| 56 | CH₃, CH₃ | CH₂C(=NOCH₂C≡CH)—CH₃ | F | S | 0 |
| 57 | CH₃, CH₃ | CH₂C(=NOCH₂C₆H₅)—CH₃ | F | S | 0 |
| 58 | CH₃, CH₃ | CH₂C(=NOCOCH₃)—CH₃ | F | S | 0 |
| 59 | CH₃, CH₃ | CH₂C(=NOSO₂CH₃)—CH₃ | F | S | 0 |
| 60 | CH₃, CH₃ | CH(CH₃)—C(=NOH)—C₂H₅ | F | S | 0 |
| 61 | CH₃, CH₃ | CH(C₂H₅)—C(=NOH)—C₃H₇ | F | S | 0 |
| 62 | CH₃, CH₃ | CH₂C(=NN(CH₃)₂)—CH₃ | F | S | 0 |
| 63 | CH₃, CH₃ | CH₂C(=NN(C₂H₅)₂)—C₂H₅ | F | S | 0 |
| 64 | CH₃, CH₃ | CH₂C(=NN(COCH₃)(CH₃))—CH₃ | F | S | 0 |
| 65 | CH₃, CH₃ | CH₂CH₂N(CH₃)₂ | F | S | 0 |
| 66 | CH₃, CH₃ | CH₂CH₂CH₂N(CH₃)₂ | F | S | 0 |

TABLE 1-continued

| 67 | CH₃, CH₃ | 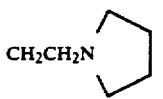 CH₂CH₂N(pyrrolidine) | F | S | 0 |
| 68 | CH₃, CH₃ | 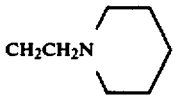 CH₂CH₂N(piperidine) | F | S | 0 |
| 69 | CH₃, CH₃ | 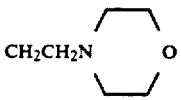 CH₂CH₂N(morpholine) | F | S | 0 |
| 70 | CH₃, CH₃ | 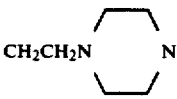 CH₂CH₂N(N-methylpiperazine)—CH₃ | F | S | 0 |
| 71 | CH₃, CH₃ | COCH₃<br>\|<br>CH₂CH₂N—C₃H₇-iso | F | S | 0 |
| 72 | CH₃, CH₃ | SO₂CH₃<br>\|<br>CH₂CH₂N—CH₃ | F | S | 0 |
| 73 | CH₃, CH₃ | CH₂COOC₂H₅ | F | S | 0 |
| 74 | CH₃, CH₃ | 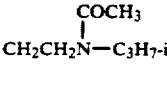 CH₂COO-cyclopentyl | F | S | 0 |
| 75 | CH₃, CH₃ | CH₃<br>\|<br>CHCOOC₂H₅ | F | S | 0 |
| 76 | CH₃, CH₃ | CH₂COOCH₂CF₃ | F | S | 0 |
| 77 | CH₃, CH₃ | CH₂CONHC₃H₇-iso | F | S | 0 |
| 78 | CH₃, CH₃ | CH₂CON(CH₃)₂ | F | S | 0 |
| 79 | CH₃, CH₃ | CH₂CON(C₃H₇-n)₂ | F | S | 0 |
| 80 | CH₃, CH₃ | 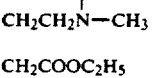 CH₂CON(piperidine) | F | S | 0 |
| 81 | CH₃, CH₃ | 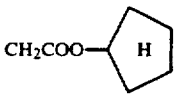 CH₃<br>\|<br>CH₂CON—C₆H₅ | F | S | 0 |
| 82 | CH₃, CH₃ |  C₃H₇-iso<br>\|<br>CH₂CON—C₆H₅ | F | S | 0 |
| 83 | CH₃, CH₃ | 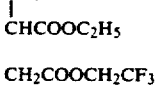 CH₃<br>\|<br>CH₂CON—(2-methylphenyl)<br>CH₃ | F | S | 0 |
| 84 | CH₃, CH₃ | 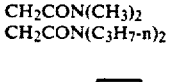 Cl<br>CH₃<br>\|<br>CH₂CON—(3-chlorophenyl) | F | S | 0 |

TABLE 1-continued

| | | | | | |
|---|---|---|---|---|---|
| 85 | $CH_3, CH_3$ | $CH_2COOCH_2Si(CH_3)_3$ | F | S | 0 |
| 86 | $CH_3, CH_3$ | $CH_2$-(1,2,4-triazol-1-yl) | F | S | 0 |
| 87 | $CH_3, CH_3$ | $CH_2$-(isoxazol-3-yl) | H | S | 0 |
| 88 | $CH_3, CH_3$ | $CH_2$-(isoxazol-4-yl) | F | S | 0 |
| 89 | $CH_3, CH_3$ | $CH_2$-(thiazol-4-yl) | F | S | 0 |
| 90 | $CH_3, CH_3$ | $CH_2$-(3-methyl-1,2,4-oxadiazol-5-yl) | F | S | 0 |
| 91 | $CH_3, CH_3$ | $CH_2$-(4-methyl-1,2,5-oxadiazol-3-yl) | F | S | 0 |
| 92 | $CH_3, CH_3$ | $CH_2$-(1,2,5-thiadiazol-3-yl) | F | S | 0 |
| 93 | $CH_3, CH_3$ | $CH_2$-(pyridin-2-yl) | H | S | 0 |
| 94 | $CH_3, CH_3$ | $CH_2$-(pyridin-3-yl) | F | S | 0 mp. 147–148° C. |
| 95 | $CH_3, CH_3$ | $CH_2$-(pyrazin-2-yl) | F | S | 0 |
| 96 | $CH_3, C_2H_5$ | H | H | S | 0 |
| 97 | $CH_3, C_2H_5$ | H | F | S | 0 |
| 98 | $CH_3, C_2H_5$ | $C_3H_7$-n | F | S | 0 |
| 99 | $CH_3, C_2H_5$ | $CH_2CH=CH_2$ | F | S | 0 |
| 100 | $CH_3, C_2H_5$ | $CH_2C\equiv CH$ | H | S | 0 |
| 101 | $CH_3, C_2H_5$ | $CH_2C\equiv CH$ | F | S | 0 Oily |
| 102 | $CH_3, C_2H_5$ | $CH_2OCH_3$ | F | S | 0 |
| 103 | $CH_3, C_2H_5$ | $CH_2SCH_3$ | F | S | 0 |
| 104 | $CH_3, C_2H_5$ | $CH_2CN$ | F | S | 0 |
| 105 | $CH_3, C_2H_5$ | $CH_2COCH_3$ | H | S | 0 |
| 106 | $CH_3, C_2H_5$ | $CH_2COCH_3$ | F | S | 0 |
| 107 | $CH_3, C_2H_5$ | $CH_2$-(isoxazol-3-yl) | H | S | 0 |

TABLE 1-continued

| # | R1, R2 | R3 | X | Y | n |
|---|---|---|---|---|---|
| 108 | CH₃, C₂H₅ | CH₂-(isoxazole) | F | S | 0 |
| 109 | CH₃, C₂H₅ | CH₂-(pyridine) | H | S | 0 |
| 110 | CH₃, C₂H₅ | CH₂-(pyridine) | F | S | 0 |
| 111 | CH₃, C₃H₇-n | H | H | S | 0 |
| 112 | CH₃, C₃H₇-n | H | F | S | 0 |
| 113 | CH₃, C₃H₇-n | C₃H₇-n | F | S | 0 |
| 114 | CH₃, C₃H₇-n | CH₂CH=CH₂ | F | S | 0 |
| 115 | CH₃, C₃H₇-n | CH₂C≡CH | H | S | 0 |
| 116 | CH₃, C₃H₇-n | CH₂C≡CH | F | S | 0 |
| 117 | CH₃, C₃H₇-n | CH₂OCH₃ | F | S | 0 |
| 118 | CH₃, C₃H₇-n | CH₂SCH₃ | F | S | 0 |
| 119 | CH₃, C₃H₇-n | CH₂CN | F | S | 0 |
| 120 | CH₃, C₃H₇-n | CH₂-(isoxazole) | H | S | 0 |
| 121 | CH₃, C₃H₇-n | CH₂-(isoxazole) | F | S | 0 |
| 122 | CH₃, C₃H₇-n | CH₂-(pyridine) | H | S | 0 |
| 123 | CH₃, C₃H₇-n | CH₂-(pyridine) | F | S | 0 |
| 124 | CH₃, C₃H₇-iso | H | H | S | 0 |
| 125 | CH₃, C₃H₇-iso | H | F | S | 0 |
| 126 | CH₃, C₃H₇-iso | C₃H₇-n | F | S | 0 |
| 127 | CH₃, C₃H₇-iso | CH₂CH=CH₂ | F | S | 0 |
| 128 | CH₃, C₃H₇-iso | CH₂C≡CH | H | S | 0 |
| 129 | CH₃, C₃H₇-iso | CH₂C≡CH | F | S | 0 |
| 130 | CH₃, C₃H₇-iso | CH₂OCH₃ | F | S | 0 |
| 131 | CH₃, C₃H₇-iso | CH₂SCH₃ | F | S | 0 |
| 132 | CH₃, C₃H₇-iso | CH₂CN | F | S | 0 |
| 133 | CH₃, C₃H₇-iso | CH₂COCH₃ | H | S | 0 |
| 134 | CH₃, C₃H₇-iso | CH₂COCH₃ | F | S | 0 |
| 135 | CH₃, C₃H₇-iso | CH₂-(isoxazole) | H | S | 0 |
| 136 | CH₃, C₃H₇-iso | CH₂-(isoxazole) | F | S | 0 |
| 137 | CH₃, C₃H₇-iso | CH₂-(pyridine) | H | S | 0 |

TABLE 1-continued

| | | | | | |
|---|---|---|---|---|---|
| 138 | CH$_3$, C$_3$H$_7$-iso | 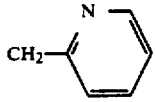 | F | S | 0 |
| 139 | CH$_3$, C$_4$H$_9$-n | H | H | S | 0 |
| 140 | CH$_3$, C$_4$H$_9$-n | H | F | S | 0 |
| 141 | CH$_3$, C$_4$H$_9$-n | C$_3$H$_7$-n | F | S | 0 |
| 142 | CH$_3$, C$_4$H$_9$-n | CH$_2$CH=CH$_2$ | F | S | 0 |
| 143 | CH$_3$, C$_4$H$_9$-n | CH$_2$C≡CH | H | S | 0 |
| 144 | CH$_3$, C$_4$H$_9$-n | CH$_2$C≡CH | F | S | 0 |
| 145 | CH$_3$, C$_4$H$_9$-n | CH$_2$OCH$_3$ | F | S | 0 |
| 146 | CH$_3$, C$_4$H$_9$-n | CH$_2$SCH$_3$ | F | S | 0 |
| 147 | CH$_3$, C$_4$H$_9$-n | CH$_2$CN | F | S | 0 |
| 148 | CH$_3$, C$_4$H$_9$-n | 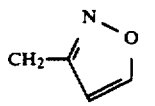 | H | S | 0 |
| 149 | CH$_3$, C$_4$H$_9$-n | 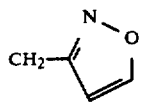 | F | S | 0 |
| 150 | CH$_3$, C$_4$H$_9$-n | 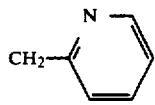 | H | S | 0 |
| 151 | CH$_3$, C$_4$H$_9$-n | 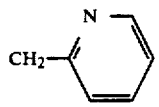 | F | S | 0 |
| 152 | CH$_3$, C$_4$H$_9$-iso | H | H | S | 0 |
| 153 | CH$_3$, C$_4$H$_9$-iso | H | F | S | 0 |
| 154 | CH$_3$, C$_4$H$_9$-iso | C$_3$H$_7$-n | F | S | 0 |
| 155 | CH$_3$, C$_4$H$_9$-iso | CH$_2$CH=CH$_2$ | F | S | 0 |
| 156 | CH$_3$, C$_4$H$_9$-iso | CH$_2$C≡CH | H | S | 0 |
| 157 | CH$_3$, C$_4$H$_9$-iso | CH$_2$C≡CH | F | S | 0 |
| 158 | CH$_3$, C$_4$H$_9$-iso | CH$_2$OCH$_3$ | F | S | 0 |
| 159 | CH$_3$, C$_4$H$_9$-iso | CH$_2$SCH$_3$ | F | S | 0 |
| 160 | CH$_3$, C$_4$H$_9$-iso | CH$_2$CN | F | S | 0 |
| 161 | CH$_3$, C$_4$H$_9$-iso | CH$_2$COCH$_3$ | H | S | 0 |
| 162 | CH$_3$, C$_4$H$_9$-iso | CH$_2$COCH$_3$ | F | S | 0 |
| 163 | CH$_3$, C$_4$H$_9$-iso | 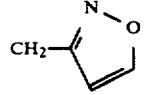 | H | S | 0 |
| 164 | CH$_3$, C$_4$H$_9$-iso | 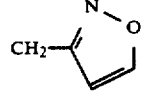 | F | S | 0 |
| 165 | CH$_3$, C$_4$H$_9$-iso | 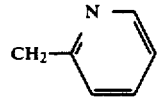 | H | S | 0 |
| 166 | CH$_3$, C$_4$H$_9$-iso | 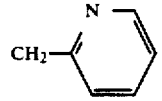 | F | S | 0 |
| 167 | CH$_3$, C$_4$H$_9$-sec | H | H | S | 0 |
| 168 | CH$_3$, C$_4$H$_9$-sec | H | F | S | 0 |
| 169 | CH$_3$, C$_4$H$_9$-sec | C$_3$H$_7$-n | F | S | 0 |
| 170 | CH$_3$, C$_4$H$_9$-sec | CH$_2$CH=CH$_2$ | F | S | 0 |
| 171 | CH$_3$, C$_4$H$_9$-sec | CH$_2$C≡CH | H | S | 0 |
| 172 | CH$_3$, C$_4$H$_9$-sec | CH$_2$C≡CH | F | S | 0 |

TABLE 1-continued

| | | | | | |
|---|---|---|---|---|---|
| 173 | CH$_3$, C$_4$H$_9$-sec | CH$_2$OCH$_3$ | F | S | 0 |
| 174 | CH$_3$, C$_4$H$_9$-sec | CH$_2$SCH$_3$ | F | S | 0 |
| 175 | CH$_3$, C$_4$H$_9$-sec | CH$_2$CN | F | S | 0 |
| 176 | CH$_3$, C$_4$H$_9$-sec | CH$_2$-isoxazolyl | H | S | 0 |
| 177 | CH$_3$, C$_4$H$_9$-sec | CH$_2$-isoxazolyl | F | S | 0 |
| 178 | CH$_3$, C$_4$H$_9$-sec | CH$_2$-pyridyl | H | S | 0 |
| 179 | CH$_3$, C$_4$H$_9$-sec | CH$_2$-pyridyl | F | S | 0 |
| 180 | CH$_3$, C$_4$H$_9$-tert | H | H | S | 0 |
| 181 | CH$_3$, C$_4$H$_9$-tert | H | F | S | 0 |
| 182 | CH$_3$, C$_4$H$_9$-tert | C$_3$H$_7$-n | F | S | 0 |
| 183 | CH$_3$, C$_4$H$_9$-tert | CH$_2$CH=CH$_2$ | F | S | 0 |
| 184 | CH$_3$, C$_4$H$_9$-tert | CH$_2$C≡CH | H | S | 0 |
| 185 | CH$_3$, C$_4$H$_9$-tert | CH$_2$C≡CH | F | S | 0 |
| 186 | CH$_3$, C$_4$H$_9$-tert | CH$_2$OCH$_3$ | F | S | 0 |
| 187 | CH$_3$, C$_4$H$_9$-tert | CH$_2$SCH$_3$ | F | S | 0 |
| 188 | CH$_3$, C$_4$H$_9$-tert | CH$_2$CN | F | S | 0 |
| 189 | CH$_3$, C$_4$H$_9$-tert | CH$_2$COCH$_3$ | H | S | 0 |
| 190 | CH$_3$, C$_4$H$_9$-tert | CH$_2$COCH$_3$ | F | S | 0 |
| 191 | CH$_3$, C$_4$H$_9$-tert | CH$_2$-isoxazolyl | H | S | 0 |
| 192 | CH$_3$, C$_4$H$_9$-tert | CH$_2$-isoxazolyl | F | S | 0 |
| 193 | CH$_3$, C$_4$H$_9$-tert | CH$_2$-pyridyl | H | S | 0 |
| 194 | CH$_3$, C$_4$H$_9$-tert | CH$_2$-pyridyl | F | S | 0 |
| 195 | C$_2$H$_5$, C$_2$H$_5$ | H | H | S | 0 |
| 196 | C$_2$H$_5$, C$_2$H$_5$ | H | F | S | 0 |
| 197 | C$_2$H$_5$, C$_2$H$_5$ | C$_3$H$_7$-n | F | S | 0 |
| 198 | C$_2$H$_5$, C$_2$H$_5$ | CH$_2$CH=CH$_2$ | F | S | 0 |
| 199 | C$_2$H$_5$, C$_2$H$_5$ | CH$_2$C≡CH | H | S | 0 |
| 200 | C$_2$H$_5$, C$_2$H$_5$ | CH$_2$C≡CH | F | S | 0 |
| 201 | C$_2$H$_5$, C$_2$H$_5$ | CH$_2$OCH$_3$ | F | S | 0 |
| 202 | C$_2$H$_5$, C$_2$H$_5$ | CH$_2$SCH$_3$ | F | S | 0 |
| 203 | C$_2$H$_5$, C$_2$H$_5$ | CH$_2$CN | F | S | 0 |
| 204 | C$_2$H$_5$, C$_2$H$_5$ | CH$_2$-isoxazolyl | H | S | 0 |

TABLE 1-continued

| | | | | | |
|---|---|---|---|---|---|
| 205 | $C_2H_5$, $C_2H_5$ | 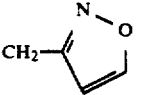 | F | S | 0 |
| 206 | $C_2H_5$, $C_2H_5$ | 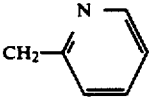 | H | S | 0 |
| 207 | $C_2H_5$, $C_2H_5$ | 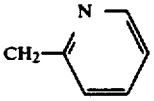 | F | S | 0 |
| 208 | $C_2H_5$, $C_3H_7$-n | H | H | S | 0 |
| 209 | $C_2H_5$, $C_3H_7$-n | H | F | S | 0 |
| 210 | $C_2H_5$, $C_3H_7$-n | $C_3H_7$-n | F | S | 0 |
| 211 | $C_2H_5$, $C_3H_7$-n | $CH_2CH=CH_2$ | F | S | 0 |
| 212 | $C_2H_5$, $C_3H_7$-n | $CH_2C\equiv CH$ | H | S | 0 |
| 213 | $C_2H_5$, $C_3H_7$-n | $CH_2C\equiv CH$ | F | S | 0 |
| 214 | $C_2H_5$, $C_3H_7$-n | $CH_2OCH_3$ | F | S | 0 |
| 215 | $C_2H_5$, $C_3H_7$-n | $CH_2SCH_3$ | F | S | 0 |
| 216 | $C_2H_5$, $C_3H_7$-n | $CH_2CN$ | F | S | 0 |
| 217 | $C_2H_5$, $C_3H_7$-n | $CH_2COCH_3$ | H | S | 0 |
| 218 | $C_2H_5$, $C_3H_7$-n | $CH_2COCH_3$ | F | S | 0 |
| 219 | $C_2H_5$, $C_3H_7$-n | 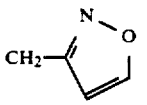 | H | S | 0 |
| 220 | $C_2H_5$, $C_3H_7$-n | 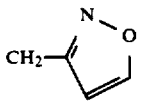 | F | S | 0 |
| 221 | $C_2H_5$, $C_3H_7$-n | 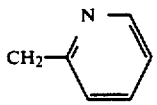 | H | S | 0 |
| 222 | $C_2H_5$, $C_3H_7$-n | 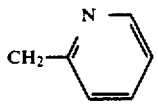 | F | S | 0 |
| 223 | $C_2H_5$, $C_3H_7$-iso | H | H | S | 0 |
| 224 | $C_2H_5$, $C_3H_7$-iso | H | F | S | 0 |
| 225 | $C_2H_5$, $C_3H_7$-iso | $C_3H_7$-n | F | S | 0 |
| 226 | $C_2H_5$, $C_3H_7$-iso | $CH_2CH=CH_2$ | F | S | 0 |
| 227 | $C_2H_5$, $C_3H_7$-iso | $CH_2C\equiv CH$ | H | S | 0 |
| 228 | $C_2H_5$, $C_3H_7$-iso | $CH_2C\equiv CH$ | F | S | 0 |
| 229 | $C_2H_5$, $C_3H_7$-iso | $CH_2OCH_3$ | F | S | 0 |
| 230 | $C_2H_5$, $C_3H_7$-iso | $CH_2SCH_3$ | F | S | 0 |
| 231 | $C_2H_5$, $C_3H_7$-iso | $CH_2CN$ | F | S | 0 |
| 232 | $C_2H_5$, $C_3H_7$-iso | 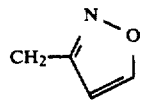 | H | S | 0 |
| 233 | $C_2H_5$, $C_3H_7$-iso | 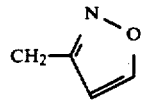 | F | S | 0 |
| 234 | $C_2H_5$, $C_3H_7$-iso | 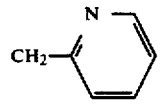 | H | S | 0 |

TABLE 1-continued

| | | | | | |
|---|---|---|---|---|---|
| 235 | C₂H₅, C₃H₇-iso | 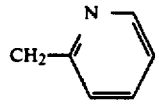 | F | S | 0 |
| 236 | C₂H₅, C₄H₉-n | H | H | S | 0 |
| 237 | C₂H₅, C₄H₉-n | H | F | S | 0 |
| 238 | C₂H₅, C₄H₉-n | C₃H₇-n | F | S | 0 |
| 239 | C₂H₅, C₄H₉-n | CH₂CH=CH₂ | F | S | 0 |
| 240 | C₂H₅, C₄H₉-n | CH₂C≡CH | H | S | 0 |
| 241 | C₂H₅, C₄H₉-n | CH₂C≡CH | F | S | 0 |
| 242 | C₂H₅, C₄H₉-n | CH₂OCH₃ | F | S | 0 |
| 243 | C₂H₅, C₄H₉-n | CH₂SCH₃ | F | S | 0 |
| 244 | C₂H₅, C₄H₉-n | CH₂CN | F | S | 0 |
| 245 | C₂H₅, C₄H₉-n | CH₂COCH₃ | H | S | 0 |
| 246 | C₂H₅, C₄H₉-n | CH₂COCH₃ | F | S | 0 |
| 247 | C₂H₅, C₄H₉-n | 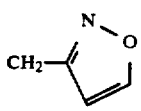 | H | S | 0 |
| 248 | C₂H₅, C₄H₉-n | 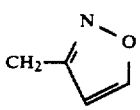 | F | S | 0 |
| 249 | C₂H₅, C₄H₉-n | 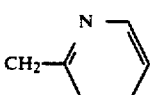 | H | S | 0 |
| 250 | C₂H₅, C₄H₉-n | 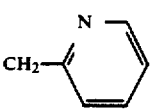 | F | S | 0 |
| 251 | C₂H₅, C₄H₉-iso | H | H | S | 0 |
| 252 | C₂H₅, C₄H₉-iso | H | F | S | 0 |
| 253 | C₂H₅, C₄H₉-iso | C₃H₇-n | F | S | 0 |
| 254 | C₂H₅, C₄H₉-iso | CH₂CH=CH₂ | F | S | 0 |
| 255 | C₂H₅, C₄H₉-iso | CH₂C≡CH | H | S | 0 |
| 256 | C₂H₅, C₄H₉-iso | CH₂C≡CH | F | S | 0 |
| 257 | C₂H₅, C₄H₉-iso | CH₂OCH₃ | F | S | 0 |
| 258 | C₂H₅, C₄H₉-iso | CH₂SCH₃ | F | S | 0 |
| 259 | C₂H₅, C₄H₉-iso | CH₂CN | F | S | 0 |
| 260 | C₂H₅, C₄H₉-iso | 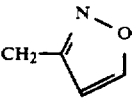 | H | S | 0 |
| 261 | C₂H₅, C₄H₉-iso | 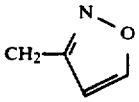 | F | S | 0 |
| 262 | C₂H₅, C₄H₉-iso | 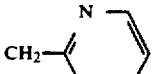 | H | S | 0 |
| 263 | C₂H₅, C₄H₉-iso | 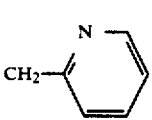 | F | S | 0 |
| 264 | C₂H₅, C₄H₉-sec | H | H | S | 0 |
| 265 | C₂H₅, C₄H₉-sec | H | F | S | 0 |
| 266 | C₂H₅, C₄H₉-sec | C₃H₇-n | F | S | 0 |
| 267 | C₂H₅, C₄H₉-sec | CH₂CH=CH₂ | F | S | 0 |
| 268 | C₂H₅, C₄H₉-sec | CH₂C≡CH | H | S | 0 |
| 269 | C₂H₅, C₄H₉-sec | CH₂C≡CH | F | S | 0 |

TABLE 1-continued

| | | | | | |
|---|---|---|---|---|---|
| 270 | $C_2H_5$, $C_4H_9$-sec | $CH_2OCH_3$ | F | S | 0 |
| 271 | $C_2H_5$, $C_4H_9$-sec | $CH_2SCH_3$ | F | S | 0 |
| 272 | $C_2H_5$, $C_4H_9$-sec | $CH_2CN$ | F | S | 0 |
| 273 | $C_2H_5$, $C_4H_9$-sec | $CH_2COCH_3$ | H | S | 0 |
| 274 | $C_2H_5$, $C_4H_9$-sec | $CH_2COCH_3$ | F | S | 0 |
| 275 | $C_2H_5$, $C_4H_9$-sec | $CH_2$-isoxazol-3-yl | H | S | 0 |
| 276 | $C_2H_5$, $C_4H_9$-sec | $CH_2$-isoxazol-3-yl | F | S | 0 |
| 277 | $C_2H_5$, $C_4H_9$-sec | $CH_2$-pyridin-2-yl | H | S | 0 |
| 278 | $C_2H_5$, $C_4H_9$-sec | $CH_2$-pyridin-2-yl | F | S | 0 |
| 279 | $C_2H_5$, $C_4H_9$-tert | H | H | S | 0 |
| 280 | $C_2H_5$, $C_4H_9$-tert | H | F | S | 0 |
| 281 | $C_2H_5$, $C_4H_9$-tert | $C_3H_7$-n | F | S | 0 |
| 282 | $C_2H_5$, $C_4H_9$-tert | $CH_2CH=CH_2$ | F | S | 0 |
| 283 | $C_2H_5$, $C_4H_9$-tert | $CH_2C\equiv CH$ | H | S | 0 |
| 284 | $C_2H_5$, $C_4H_9$-tert | $CH_2C\equiv CH$ | F | S | 0 |
| 285 | $C_2H_5$, $C_4H_9$-tert | $CH_2OCH_3$ | F | S | 0 |
| 286 | $C_2H_5$, $C_4H_9$-tert | $CH_2SCH_3$ | F | S | 0 |
| 287 | $C_2H_5$, $C_4H_9$-tert | $CH_2CN$ | F | S | 0 |
| 288 | $C_2H_5$, $C_4H_9$-tert | $CH_2$-isoxazol-3-yl | H | S | 0 |
| 289 | $C_2H_5$, $C_4H_9$-tert | $CH_2$-isoxazol-3-yl | F | S | 0 |
| 290 | $C_2H_5$, $C_4H_9$-tert | $CH_2$-pyridin-2-yl | H | S | 0 |
| 291 | $C_2H_5$, $C_4H_9$-tert | $CH_2$-pyridin-2-yl | F | S | 0 |
| 292 | $C_3H_7$-n, $C_3H_7$-n | H | H | S | 0 |
| 293 | $C_3H_7$-n, $C_3H_7$-n | H | F | S | 0 |
| 294 | $C_3H_7$-n, $C_3H_7$-n | $C_3H_7$-n | F | S | 0 |
| 295 | $C_3H_7$-n, $C_3H_7$-n | $CH_2CH=CH_2$ | F | S | 0 |
| 296 | $C_3H_7$-n, $C_3H_7$-n | $CH_2C\equiv CH$ | H | S | 0 |
| 297 | $C_3H_7$-n, $C_3H_7$-n | $CH_2C\equiv CH$ | F | S | 0 |
| 298 | $C_3H_7$-n, $C_3H_7$-n | $CH_2OCH_3$ | F | S | 0 |
| 299 | $C_3H_7$-n, $C_3H_7$-n | $CH_2SCH_3$ | F | S | 0 |
| 300 | $C_3H_7$-n, $C_3H_7$-n | $CH_2CN$ | F | S | 0 |
| 301 | $C_3H_7$-n, $C_3H_7$-n | $CH_2COCH_3$ | H | S | 0 |
| 302 | $C_3H_7$-n, $C_3H_7$-n | $CH_2COCH_3$ | F | S | 0 |
| 303 | $C_3H_7$-n, $C_3H_7$-n | $CH_2$-isoxazol-3-yl | H | S | 0 |

TABLE 1-continued

| | | | | | |
|---|---|---|---|---|---|
| 304 | C$_3$H$_7$-n, C$_3$H$_7$-n | (isoxazole-CH$_2$-) | F | S | 0 |
| 305 | C$_3$H$_7$-n, C$_3$H$_7$-n | (pyridine-CH$_2$-) | H | S | 0 |
| 306 | C$_3$H$_7$-n, C$_3$H$_7$-n | (pyridine-CH$_2$-) | F | S | 0 |
| 307 | C$_3$H$_7$-n, C$_4$H$_9$-n | CH$_2$C≡CH | F | S | 0 |
| 308 | C$_3$H$_7$-n, C$_4$H$_9$-n | CH$_2$COCH$_3$ | F | S | 0 |
| 309 | C$_3$H$_7$-n, C$_4$H$_9$-iso | CH$_2$C≡CH | F | S | 0 |
| 310 | C$_3$H$_7$-n, C$_4$H$_9$-iso | CH$_2$COCH$_3$ | F | S | 0 |
| 311 | C$_3$H$_7$-n, C$_4$H$_9$-sec | CH$_2$C≡CH | F | S | 0 |
| 312 | C$_3$H$_7$-n, C$_4$H$_9$-sec | CH$_2$COCH$_3$ | F | S | 0 |
| 313 | C$_3$H$_7$-n, C$_4$H$_9$-tert | CH$_2$C≡CH | F | S | 0 |
| 314 | C$_3$H$_7$-n, C$_4$H$_9$-tert | CH$_2$COCH$_3$ | F | S | 0 |
| 315 | C$_4$H$_9$-n, C$_4$H$_9$-n | CH$_2$C≡CH | F | S | 0 |
| 316 | C$_4$H$_9$-n, C$_4$H$_9$-n | CH$_2$COCH$_3$ | F | S | 0 |
| 317 | C$_4$H$_9$-n, C$_4$H$_9$-iso | CH$_2$C≡CH | F | S | 0 |
| 318 | C$_4$H$_9$-n, C$_4$H$_9$-iso | CH$_2$COCH$_3$ | F | S | 0 |
| 319 | C$_4$H$_9$-n, C$_4$H$_9$-sec | CH$_2$C≡CH | F | S | 0 |
| 320 | C$_4$H$_9$-n, C$_4$H$_9$-sec | CH$_2$COCH$_3$ | F | S | 0 |
| 321 | —(CH$_2$)$_4$— | H | F | S | 0 mp. 218–223° C. |
| 322 | —(CH$_2$)$_4$— | CH$_3$ | F | S | 0 |
| 323 | —(CH$_2$)$_4$— | C$_2$H$_5$ | F | S | 0 |
| 324 | —(CH$_2$)$_4$— | C$_3$H$_7$-n | F | S | 0 |
| 325 | —(CH$_2$)$_4$— | C$_4$H$_9$-n | F | S | 0 |
| 326 | —(CH$_2$)$_4$— | C$_4$H$_9$-iso | F | S | 0 |
| 327 | —(CH$_2$)$_4$— | C$_4$H$_9$-sec | F | S | 0 |
| 328 | —(CH$_2$)$_4$— | CH$_2$CH$_2$F | F | S | 0 |
| 329 | —(CH$_2$)$_4$— | CH$_2$CH$_2$CH$_2$Cl | F | S | 0 |
| 330 | —(CH$_2$)$_4$— | CH$_2$-cyclopropyl | F | S | 0 |
| 331 | —(CH$_2$)$_4$— | CH$_2$CH=CH$_2$ | F | S | 0 |
| 332 | —(CH$_2$)$_4$— | CH$_2$CH$_2$CH=CH$_2$ | F | S | 0 |
| 333 | —(CH$_2$)$_4$— | CH$_2$CCl=CH$_2$ | F | S | 0 |
| 334 | —(CH$_2$)$_4$— | CH$_2$CH=CHCl | F | S | 0 |
| 335 | —(CH$_2$)$_4$— | CH$_2$CCl=CHCl | F | S | 0 |
| 336 | —(CH$_2$)$_4$— | CH$_2$CCl=CCl$_2$ | F | S | 0 |
| 337 | —(CH$_2$)$_4$— | CH$_2$C≡CH | H | S | 0 |
| 338 | —(CH$_2$)$_4$— | CH$_2$C≡CH | F | S | 0 mp. 139–140.5° C. |
| 339 | —(CH$_2$)$_4$— | CH(CH$_3$)C≡CH | F | S | 0 |
| 340 | —(CH$_2$)$_4$— | CH$_2$OCH$_3$ | F | S | 0 |
| 341 | —(CH$_2$)$_4$— | CH$_2$OC$_2$H$_5$ | F | S | 0 |
| 342 | —(CH$_2$)$_4$— | CH$_2$CH$_2$OC$_2$H$_5$ | F | S | 0 |
| 343 | —(CH$_2$)$_4$— | CH$_2$SCH$_3$ | F | S | 0 |
| 344 | —(CH$_2$)$_4$— | CH$_2$SC$_2$H$_5$ | F | S | 0 |
| 345 | —(CH$_2$)$_4$— | CH$_2$CH$_2$SC$_2$H$_5$ | F | S | 0 |
| 346 | —(CH$_2$)$_4$— | CH$_2$S(O)CH$_3$ | F | S | 0 |

-continued

| | | | | | |
|---|---|---|---|---|---|
| 347 | —(CH$_2$)$_4$— | $\underset{\overset{\|}{O}}{\overset{O}{\underset{\|}{CH_2\overset{\|}{S}CH_3}}}$ | F | S | 0 |
| 348 | —(CH$_2$)$_4$— | CH$_2$S—C$_6$H$_5$ | F | S | 0 |
| 349 | —(CH$_2$)$_4$— | CH$_2$S—C$_6$H$_4$—Cl | F | S | 0 |
| 350 | —(CH$_2$)$_4$— | CH$_2$S(O)—C$_6$H$_5$ | F | S | 0 |
| 351 | —(CH$_2$)$_4$— | CH$_2$S(O)$_2$—C$_6$H$_5$ | F | S | 0 |
| 352 | —(CH$_2$)$_4$— | CH$_2$CN | F | S | 0 |
| 353 | —(CH$_2$)$_4$— | CH(CH$_3$)CN | F | S | 0 |
| 354 | —(CH$_2$)$_4$— | CH$_2$CONH$_2$ | F | S | 0 |
| 355 | —(CH$_2$)$_4$— | CH$_2$CSNH$_2$ | F | S | 0 |
| 356 | —(CH$_2$)$_4$— | CH$_2$Si(CH$_3$)$_3$ | F | S | 0 |
| 357 | —(CH$_2$)$_4$— | CH$_2$—C$_6$H$_5$ | F | S | 0 |
| 358 | —(CH$_2$)$_4$— | CH$_2$—C$_6$H$_4$—CH$_3$ | F | S | 0 |
| 359 | —(CH$_2$)$_4$— | CH$_2$—C$_6$H$_4$—OCH$_3$ | F | S | 0 |
| 360 | —(CH$_2$)$_4$— | CH$_2$—C$_6$H$_4$—Cl | F | S | 0 |
| 361 | —(CH$_2$)$_4$— | CH$_2$—C$_6$H$_4$—F | F | S | 0 |
| 362 | —(CH$_2$)$_4$— | CH$_2$COCH$_3$ | H | S | 0 |
| 363 | —(CH$_2$)$_4$— | CH$_2$COCH$_3$ | F | S | 0 |
| 364 | —(CH$_2$)$_4$— | CH$_2$COC$_2$H$_5$ | F | S | 0 |
| 365 | —(CH$_2$)$_4$— | CH(CH$_3$)COC$_2$H$_5$ | F | S | 0 |
| 366 | —(CH$_2$)$_4$— | CH(C$_2$H$_5$)COC$_3$H$_7$ | F | S | 0 |

-continued

| # | | | | | |
|---|---|---|---|---|---|
| 367 | —(CH$_2$)$_4$— | CH$_2$O—C$_6$H$_5$ | F | S | 0 |
| 368 | —(CH$_2$)$_4$— | CH$_2$O—C$_6$H$_4$—CH$_3$ (4-) | F | S | 0 |
| 369 | —(CH$_2$)$_4$— | CH$_2$—CO—C$_6$H$_4$—Cl (4-) | F | S | 0 |
| 370 | —(CH$_2$)$_4$— | CH$_2$C(=N—OH)—CH$_3$ | F | S | 0 |
| 371 | —(CH$_2$)$_4$— | CH$_2$—C(=N—OH)—C$_6$H$_5$ | F | S | 0 |
| 372 | —(CH$_2$)$_4$— | CH$_2$C(=N—OCH$_3$)—CH$_3$ | F | S | 0 |
| 373 | —(CH$_2$)$_4$— | CH$_2$—C(=N—OCH$_3$)—C$_6$H$_5$ | F | S | 0 |
| 374 | —(CH$_2$)$_4$— | CH$_2$C(=N—OC$_2$H$_5$)—CH$_3$ | F | S | 0 |
| 375 | —(CH$_2$)$_4$— | CH$_2$C(=N—OCH$_2$CH=CH$_2$)—CH$_3$ | F | S | 0 |
| 376 | —(CH$_2$)$_4$— | CH$_2$C(=N—OCH$_2$C≡CH)—CH$_3$ | F | S | 0 |
| 377 | —(CH$_2$)$_4$— | CH$_2$C(=N—OCH$_2$C$_6$H$_5$)—CH$_3$ | F | S | 0 |
| 378 | —(CH$_2$)$_4$— | CH$_2$C(=N—OCOCH$_3$)—CH$_3$ | F | S | 0 |
| 379 | —(CH$_2$)$_4$— | CH$_2$C(=N—OSO$_2$CH$_3$)—CH$_3$ | F | S | 0 |
| 380 | —(CH$_2$)$_4$— | CH(CH$_3$)—C(=N—OH)—C$_2$H$_5$ | F | S | 0 |
| 381 | —(CH$_2$)$_4$— | CH(C$_2$H$_5$)—C(=N—OH)—C$_3$H$_7$ | F | S | 0 |
| 382 | —(CH$_2$)$_4$— | CH$_2$C(=NN(CH$_3$)$_2$)—CH$_3$ | F | S | 0 |

| | | -continued | | | |
|---|---|---|---|---|---|
| 383 | —(CH$_2$)$_4$— | CH$_2$C(=NN(C$_2$H$_5$)$_2$)—C$_2$H$_5$ | F | S | 0 |
| 384 | —(CH$_2$)$_4$— | CH$_2$C(=N—N(COCH$_3$)(CH$_3$))—CH$_3$ | F | S | 0 |
| 385 | —(CH$_2$)$_4$— | CH$_2$CH$_2$N(CH$_3$)$_2$ | F | S | 0 |
| 386 | —(CH$_2$)$_4$— | CH$_2$CH$_2$CH$_2$N(CH$_3$)$_2$ | F | S | 0 |
| 387 | —(CH$_2$)$_4$— | CH$_2$CH$_2$N(pyrrolidine) | F | S | 0 |
| 388 | —(CH$_2$)$_4$— | CH$_2$CH$_2$N(piperidine) | F | S | 0 |
| 389 | —(CH$_2$)$_4$— | CH$_2$CH$_2$N(morpholine) | F | S | 0 |
| 390 | —(CH$_2$)$_4$— | CH$_2$CH$_2$N(N-methylpiperazine) | F | S | 0 |
| 391 | —(CH$_2$)$_4$— | CH$_2$CH$_2$N(COCH$_3$)—C$_3$H$_7$-iso | F | S | 0 |
| 392 | —(CH$_2$)$_4$— | CH$_2$CH$_2$N(SO$_2$CH$_3$)—CH$_3$ | F | S | 0 |
| 393 | —(CH$_2$)$_4$— | CH$_2$COOC$_2$H$_5$ | F | S | 0 |
| 394 | —(CH$_2$)$_4$— | CH$_2$COO-cyclopentyl | F | S | 0 |
| 395 | —(CH$_2$)$_4$— | CH(CH$_3$)COOC$_2$H$_5$ | F | S | 0 |
| 396 | —(CH$_2$)$_4$— | CH$_2$COOCH$_2$CF$_3$ | F | S | 0 |
| 397 | —(CH$_2$)$_4$— | CH$_2$CONHC$_3$H$_7$-iso | F | S | 0 |
| 398 | —(CH$_2$)$_4$— | CH$_2$CON(CH$_3$)$_2$ | F | S | 0 |
| 399 | —(CH$_2$)$_4$— | CH$_2$CON(C$_3$H$_7$-n)$_2$ | F | S | 0 |
| 400 | —(CH$_2$)$_4$— | CH$_2$CON(piperidine) | F | S | 0 |
| 401 | —(CH$_2$)$_4$— | CH$_2$CON(CH$_3$)(C$_6$H$_5$) | F | S | 0 |
| 402 | —(CH$_2$)$_4$— | CH$_2$CON(C$_3$H$_7$-iso)(C$_6$H$_5$) | F | S | 0 |

-continued
| | | | | | | |
|---|---|---|---|---|---|---|
| 403 | —(CH₂)₄— | 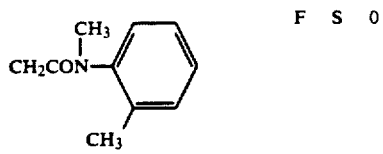 | F | S | 0 | |
| 404 | —(CH₂)₄— | 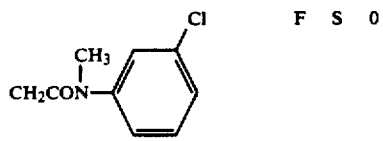 | F | S | 0 | |
| 405 | —(CH₂)₄— | CH₂COOCH₂Si(CH₃)₃ | F | S | 0 | |
| 406 | —(CH₂)₄— | 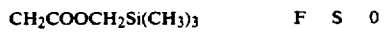 | F | S | 0 | |
| 407 | —(CH₂)₄— |  | H | S | 0 | |
| 408 | —(CH₂)₄— |  | F | S | 0 | mp. 177–181° C. |
| 409 | —(CH₂)₄— |  | F | S | 0 | mp. 143–149° C. |
| 410 | —(CH₂)₄— |  | F | S | 0 | mp. 153–155° C. |
| 411 | —(CH₂)₄— | 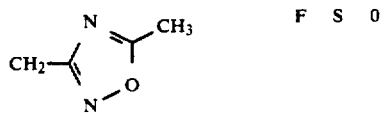 | F | S | 0 | |
| 412 | —(CH₂)₄— | 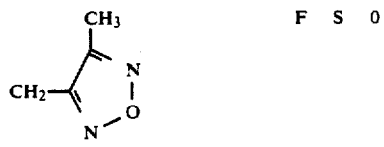 | F | S | 0 | |
| 413 | —(CH₂)₄— |  | H | S | 0 | |
| 414 | —(CH₂)₄— | 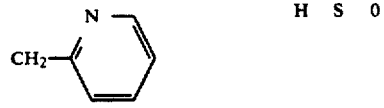 | F | S | 0 | |
| 415 | —(CH₂)₄— | 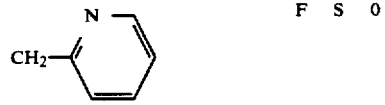 | F | S | 0 | |

| | | | | | | |
|---|---|---|---|---|---|---|
| 416 | —(CH$_2$)$_4$— | 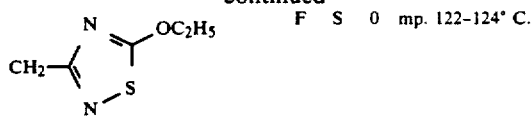 | F | S | 0 | mp. 122–124° C. |
| 417 | CH$_3$, CH$_3$ | H | H | O | 0 | |
| 418 | CH$_3$, CH$_3$ | H | F | O | 0 | |
| 419 | CH$_3$, CH$_3$ | C$_3$H$_7$-n | F | O | 0 | |
| 420 | CH$_3$, CH$_3$ | CH$_2$CH=CH$_2$ | F | O | 0 | |
| 421 | CH$_3$, CH$_3$ | CH$_2$C≡CH | H | O | 0 | |
| 422 | CH$_3$, CH$_3$ | CH$_2$C≡CH | F/O | | 0 | |
| 423 | CH$_3$, CH$_3$ | CH$_2$OCH$_3$ | F | O | 0 | |
| 424 | CH$_3$, CH$_3$ | CH$_2$SCH$_3$ | F | O | 0 | |
| 425 | CH$_3$, CH$_3$ | CH$_2$CN | F | O | 0 | |
| 426 | CH$_3$, CH$_3$ | CH$_2$OCH$_3$ | H | O | 0 | |
| 427 | CH$_3$, CH$_3$ | CH$_2$COCH$_3$ | F | O | 0 | |
| 428 | CH$_3$, CH$_3$ | 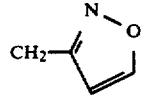 | H | O | 0 | |
| 429 | CH$_3$, CH$_3$ | 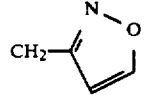 | F | O | 0 | |
| 430 | CH$_3$, CH$_3$ | 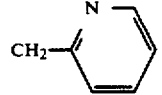 | H | O | 0 | |
| 431 | CH$_3$, CH$_3$ | 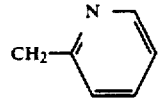 | F | O | 0 | |
| 432 | —(CH$_2$)$_4$— | H | H | O | 0 | |
| 433 | —(CH$_2$)$_4$— | H | F | O | 0 | |
| 434 | —(CH$_2$)$_4$— | C$_3$H$_7$-n | F | O | 0 | |
| 435 | —(CH$_2$)$_4$— | CH$_2$CH=CH$_2$ | F | O | 0 | |
| 436 | —(CH$_2$)$_4$— | CH$_2$C≡CH | H | O | 0 | |
| 437 | —(CH$_2$)$_4$— | CH$_2$C≡CH | F | O | 0 | |
| 438 | —(CH$_2$)$_4$— | CH$_2$OCH$_3$ | F | O | 0 | |
| 439 | —(CH$_2$)$_4$— | CH$_2$SCH$_3$ | F | O | 0 | |
| 440 | —(CH$_2$)$_4$— | CH$_2$CN | F | O | 0 | |
| 441 | —(CH$_2$)$_4$— | CH$_2$COCH$_3$ | H | O | 0 | |
| 442 | —(CH$_2$)$_4$— | CH$_2$COCH$_3$ | F | O | 0 | |
| 443 | —(CH$_2$)$_4$— | 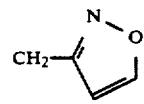 | H | O | 0 | |
| 444 | —(CH$_2$)$_4$— | 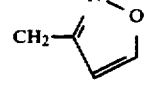 | F | O | 0 | mp. 132–136° C. |
| 445 | —(CH$_2$)$_4$— | 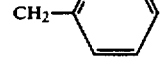 | H | O | 0 | |
| 446 | —(CH$_2$)$_4$— | 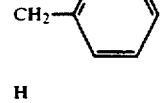 | F | O | 0 | |
| 447 | CH$_3$, C$_2$H$_5$ | H | F | O | 0 | |
| 448 | CH$_3$, C$_2$H$_5$ | CH$_2$C≡CH | F | O | 0 | Oily |
| 449 | CH$_3$, C$_2$H$_5$ | CH$_2$COCH$_3$ | F | O | 0 | |

-continued

| No. | R1, R2 | R3 | | | | Notes |
|---|---|---|---|---|---|---|
| 450 | CH3, C2H5 | -CH2-(3-isoxazolyl) | F | O | 0 | |
| 451 | CH3, C3H7-n | H | F | O | 0 | |
| 452 | CH3, C3H7-n | CH2C≡CH | F | O | 0 | |
| 453 | CH3, C3H7-n | CH2COCH3 | F | O | 0 | |
| 454 | CH3, C3H7-n | -CH2-(3-isoxazolyl) | F | O | 0 | |
| 455 | C2H5, C2H5 | H | F | O | 0 | |
| 456 | C2H5, C2H5 | C3H7-n | F | O | 0 | |
| 457 | C2H5, C2H5 | CH2C≡CH | F | O | 0 | |
| 458 | C2H5, C2H5 | CH2SCH3 | F | O | 0 | |
| 459 | C2H5, C2H5 | CH2COCH3 | F | O | 0 | |
| 460 | C2H5, C2H5 | -CH2-(3-isoxazolyl) | F | O | 1 | |
| 461 | C2H5, C2H5 | -CH2-(2-pyridyl) | F | O | 1 | |
| 462 | C2H5, C3H7-n | H | F | O | 1 | |
| 463 | C2H5, C3H7-n | CH2C≡CH | F | O | 1 | |
| 464 | C2H5, C3H7-n | CH2COCH3 | F | O | 1 | |
| 465 | C3H7, C3H7-n | H | F | O | 1 | |
| 466 | C3H7-n, C3H7-n | CH2C≡CH | F | O | 1 | |
| 467 | C3H7-n, C3H7-n | CH2COCH3 | F | O | 1 | |
| 468 | C3H7-iso, CH3 | CH2C≡CH | F | O | 1 | |
| 469 | C3H7-iso, CH3 | CH2COCH3 | F | O | 1 | |
| 470 | C3H7-iso, C3H7-iso | CH2C≡CH | F | O | 1 | |
| 471 | C3H7-iso, C3H7-iso | CH2COCH3 | F | O | 1 | |
| 472 | C4H9-n, C4H9-n | CH2C≡CH | F | O | 1 | |
| 473 | CH3, CH3 | H | F | O | 1 | mp. 238-240° C. |
| 474 | CH3, CH3 | CH3 | F | O | 1 | |
| 475 | CH3, CH3 | C2H5 | F | O | 1 | |
| 476 | CH3, CH3 | C3H7-n | F | O | 1 | |
| 477 | CH3, CH3 | C4H9-n | F | O | 1 | |
| 478 | CH3, CH3 | C4H9-iso | F | O | 1 | |
| 479 | CH3, CH3 | C4H9-sec | F | O | 1 | |
| 480 | CH3, CH3 | CH2CH2F | F | O | 1 | |
| 481 | CH3, CH3 | CH2CH2CH2Cl | F | O | 1 | |
| 482 | CH3, CH3 | -CH2-cyclopropyl | F | O | 1 | |
| 483 | CH3, CH3 | CH2CH=CH2 | F | O | 1 | |
| 484 | CH3, CH3 | CH2CH2CH=CH2 | F | O | 1 | |
| 485 | CH3, CH3 | CH2CCl=CH2 | F | O | 1 | |
| 486 | CH3, CH3 | CH2CH=CHCl | F | O | 1 | |
| 487 | CH3, CH3 | CH2CCl=CHCl | F | O | 1 | |
| 488 | CH3, CH3 | CH2CCl=CCl2 | F | O | 1 | |
| 489 | CH3, CH3 | CH2C≡CH | H | O | 1 | |
| 490 | CH3, CH3 | CH2C≡CH | F | O | 1 | mp. 123-125° C. |
| 491 | CH3, CH3 | CH(CH3)C≡CH | F | O | 1 | |
| 492 | CH3, CH3 | CH2OCH3 | F | O | 1 | |

-continued

| | | | | | |
|---|---|---|---|---|---|
| 493 | CH₃, CH₃ | CH₂OC₂H₅ | F | O | 1 |
| 494 | CH₃, CH₃ | CH₂CH₂OC₂H₅ | F | O | 1 |
| 495 | CH₃, CH₃ | CH₂SCH₃ | F | O | 1 |
| 496 | CH₃, CH₃ | CH₂SC₂H₅ | F | O | 1 |
| 497 | CH₃, CH₃ | CH₂CH₂SC₂H₅ | F | O | 1 |
| 498 | CH₃, CH₃ | $\mathrm{CH_2\overset{\displaystyle O}{\overset{\|}{S}}CH_3}$ | F | O | 1 |
| 499 | CH₃, CH₃ | $\mathrm{CH_2\overset{\displaystyle O}{\overset{\|}{\underset{\underset{\displaystyle O}{\|}{S}}{}}}CH_3}$ | F | O | 1 |
| 500 | CH₃, CH₃ | CH₂S—C₆H₅ | F | O | 1 |
| 501 | CH₃, CH₃ | CH₂S—C₆H₄—Cl | F | O | 1 |
| 502 | CH₃, CH₃ | CH₂S(O)—C₆H₅ | F | O | 1 |
| 503 | CH₃, CH₃ | CH₂S(O)₂—C₆H₅ | F | O | 1 |
| 504 | CH₃, CH₃ | CH₂CN | F | O | 1 |
| 505 | CH₃, CH₃ | CH(CH₃)—CN | F | O | 1 |
| 506 | CH₃, CH₃ | CH₂CONH₂ | F | O | 1 |
| 507 | CH₃, CH₃ | CH₂CSNH₂ | F | O | 1 |
| 508 | CH₃, CH₃ | CH₂Si(CH₃)₃ | F | O | 1 |
| 509 | CH₃, CH₃ | CH₂—C₆H₅ | F | O | 1 |
| 510 | CH₃, CH₃ | CH₂—C₆H₄—CH₃ | F | O | 1 |
| 511 | CH₃, CH₃ | CH₂—C₆H₄—OCH₃ | F | O | 1 |
| 512 | CH₃, CH₃ | CH₂—C₆H₄—Cl | F | O | 1 |
| 513 | CH₃, CH₃ | CH₂—C₆H₄—F | F | O | 1 |
| 514 | CH₃, CH₃ | CH₂COCH₃ | H | O | 1 |
| 515 | CH₃, CH₃ | CH₂COCH₃ | F | O | 1 |

-continued

| | | | | | |
|---|---|---|---|---|---|
| 516 | CH₃, CH₃ | CH₂COC₂H₅ | F | O | 1 |
| 517 | CH₃, CH₃ | CH₃–CHCOC₂H₅ | F | O | 1 |
| 518 | CH₃, CH₃ | C₂H₅–CHCOC₃H₇ | F | O | 1 |
| 519 | CH₃, CH₃ | CH₂CO–C₆H₅ | F | O | 1 |
| 520 | CH₃, CH₃ | CH₂CO–C₆H₄–CH₃ | F | O | 1 |
| 521 | CH₃, CH₃ | CH₂–CO–C₆H₄–Cl | F | O | 1 |
| 522 | CH₃, CH₃ | CH₂C(=N–OH)–CH₃ | F | O | 1 |
| 523 | CH₃, CH₃ | CH₂C(=N–OH)–C₆H₅ | F | O | 1 |
| 524 | CH₃, CH₃ | CH₂C(=N–OCH₃)–CH₃ | F | O | 1 |
| 525 | CH₃, CH₃ | CH₂C(=N–OCH₃)–C₆H₅ | F | O | 1 |
| 526 | CH₃, CH₃ | CH₂C(=N–OC₂H₅)–CH₃ | F | O | 1 |
| 527 | CH₃, CH₃ | CH₂C(=N–OCH₂CH=CH₂)–CH₃ | F | O | 1 |
| 528 | CH₃, CH₃ | CH₂C(=N–OCH₂C≡CH)–CH₃ | F | O | 1 |
| 529 | CH₃, CH₃ | CH₂C(=N–OCH₂C₆H₅)–CH₃ | F | O | 1 |
| 530 | CH₃, CH₃ | CH₂C(=N–OCOCH₃)–CH₃ | F | O | 1 |
| 531 | CH₃, CH₃ | CH₂C(=N–OSO₂CH₃)–CH₃ | F | O | 1 |
| 532 | CH₃, CH₃ | CH₃–CH–C(=N–OH)–C₂H₅ | F | O | 1 |

-continued

| No. | | | | | |
|---|---|---|---|---|---|
| 533 | CH₃, CH₃ | CH–C(=N–OH)(C₃H₇) with C₂H₅ on CH | F | O | 1 |
| 534 | CH₃, CH₃ | CH₂C(=NN(CH₃)₂)CH₃ | F | O | 1 |
| 535 | CH₃, CH₃ | CH₂C(=NN(C₂H₅)₂)C₂H₅ | F | O | 1 |
| 536 | CH₃, CH₃ | CH₂C(=NN(COCH₃)(CH₃))CH₃ | F | O | 1 |
| 537 | CH₃, CH₃ | CH₂CH₂N(CH₃)₂ | F | O | 1 |
| 538 | CH₃, CH₃ | CH₂CH₂CH₂N(CH₃)₂ | F | O | 1 |
| 539 | CH₃, CH₃ | CH₂CH₂N-pyrrolidinyl | F | O | 1 |
| 540 | CH₃, CH₃ | CH₂CH₂N-piperidinyl | F | O | 1 |
| 541 | CH₃, CH₃ | CH₂CH₂N-morpholinyl | F | O | 1 |
| 542 | CH₃, CH₃ | CH₂CH₂N(N-methylpiperazinyl) | F | O | 1 |
| 543 | CH₃, CH₃ | CH₂CH₂N(COCH₃)(C₃H₇-iso) | F | O | 1 |
| 544 | CH₃, CH₃ | CH₂CH₂N(SO₂CH₃)(CH₃) | F | O | 1 |
| 545 | CH₃, CH₃ | CH₂COOC₂H₅ | F | O | 1 |
| 546 | CH₃, CH₃ | CH₂COO-cyclopentyl | F | O | 1 |
| 547 | CH₃, CH₃ | CH(CH₃)COOC₂H₅ | F | O | 1 |
| 548 | CH₃, CH₃ | CH₂COOCH₂CF₃ | F | O | 1 |
| 549 | CH₃, CH₃ | CH₂CONHC₃H₇-iso | F | O | 1 |
| 550 | CH₃, CH₃ | CH₂CON(CH₃)₂ | F | O | 1 |
| 551 | CH₃, CH₃ | CH₂CON(C₃H₇-n)₂ | F | O | 1 |
| 552 | CH₃, CH₃ | CH₂CON-piperidinyl | F | O | 1 |
| 553 | CH₃, CH₃ | CH₂CON(CH₃)(C₆H₅) | F | O | 1 |

| | | | | | |
|---|---|---|---|---|---|
| 554 | CH₃, CH₃ | 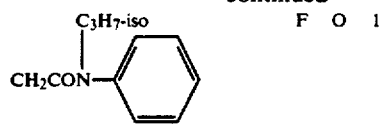 | F | O | 1 |
| 555 | CH₃, CH₃ | 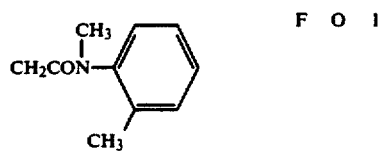 | F | O | 1 |
| 556 | CH₃, CH₃ | 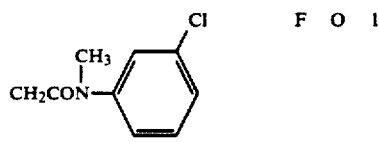 | F | O | 1 |
| 557 | CH₃, CH₃ | CH₂COOCH₂Si(CH₃)₃ | F | O | 1 |
| 558 | CH₃, CH₃ | 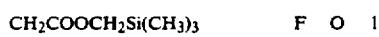 | F | O | 1 |
| 559 | CH₃, CH₃ |  | H | O | 1 |
| 560 | CH₃, CH₃ |  | F | O | 1 |
| 561 | CH₃, CH₃ |  | F | O | 1 |
| 562 | CH₃, CH₃ | 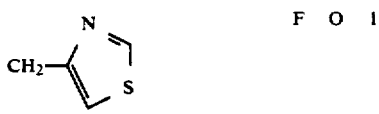 | F | O | 1 |
| 563 | CH₃, CH₃ | 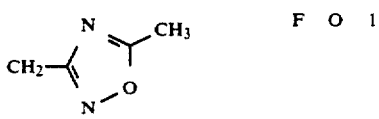 | F | O | 1 |
| 564 | CH₃, CH₃ |  | F | O | 1 |
| 565 | CH₃, CH₃ | 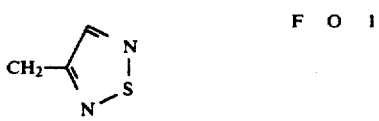 | H | O | 1 |
| 566 | CH₃, CH₃ | 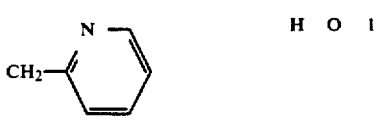 | F | O | 1 |

| | | | | | |
|---|---|---|---|---|---|
| 567 | CH₃, CH₃ | 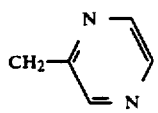 | F | O | 1 |
| 568 | CH₃, C₂H₅ | H | H | O | 1 |
| 569 | CH₃, C₂H₅ | H | F | O | 1 |
| 570 | CH₃, C₂H₅ | C₃H₇-n | F | O | 1 |
| 571 | CH₃, C₂H₅ | CH₂CH=CH₂ | F | O | 1 |
| 572 | CH₃, C₂H₅ | CH₂C≡CH | H | O | 1 |
| 573 | CH₃, C₂H₅ | CH₂C≡CH | F | O | 1 Oily |
| 574 | CH₃, C₂H₅ | CH₂OCH₃ | F | O | 1 |
| 575 | CH₃, C₂H₅ | CH₂SCH₃ | F | O | 1 |
| 576 | CH₃, C₂H₅ | CH₂CN | F | O | 1 |
| 577 | CH₃, C₂H₅ | CH₂COCH₃ | H | O | 1 |
| 578 | CH₃, C₂H₅ | CH₂COCH₃ | F | O | 1 |
| 579 | CH₃, C₂H₅ | 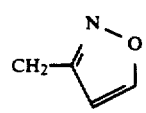 | H | O | 1 |
| 580 | CH₃, C₂H₅ | 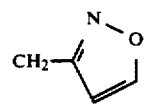 | F | O | 1 |
| 581 | CH₃, C₂H₅ | 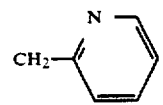 | H | O | 1 |
| 582 | CH₃, C₂H₅ | 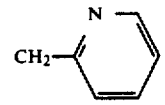 | F | O | 1 |
| 583 | CH₃, C₃H₇-n | H | H | O | 1 |
| 584 | CH₃, C₃H₇-n | H | F | O | 1 |
| 585 | CH₃, C₃H₇-n | C₃H₇-n | F | O | 1 |
| 586 | CH₃, C₃H₇-n | CH₂CH=CH₂ | F | O | 1 |
| 587 | CH₃, C₃H₇-n | CH₂C≡CH | H | O | 1 |
| 588 | CH₃, C₃H₇-n | CH₂C≡CH | F | O | 1 |
| 589 | CH₃, C₃H₇-n | CH₂OCH₃ | F | O | 1 |
| 590 | CH₃, C₃H₇-n | CH₂SCH₃ | F | O | 1 |
| 591 | CH₃, C₃H₇-n | CH₂CN | F | O | 1 |
| 592 | CH₃, C₃H₇-n | 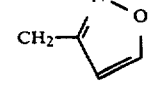 | H | O | 1 |
| 593 | CH₃, C₃H₇-n | 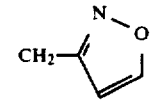 | F | O | 1 |
| 594 | CH₃, C₃H₇-n | 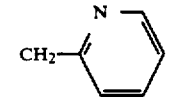 | H | O | 1 |
| 595 | CH₃, C₃H₇-n | 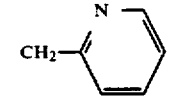 | F | O | 1 |
| 596 | CH₃, C₃H₇-iso | H | H | O | 1 |
| 597 | CH₃, C₃H₇-iso | H | F | O | 1 |
| 598 | CH₃, C₃H₇-iso | C₃H₇-n | F | O | 1 |
| 599 | CH₃, C₃H₇-iso | CH₂CH=CH₂ | F | O | 1 |
| 600 | CH₃, C₃H₇-iso | CH₂C≡CH | H | O | 1 |
| 601 | CH₃, C₃H₇-iso | CH₂C≡CH | F | O | 1 |
| 602 | CH₃, C₃H₇-iso | CH₂OCH₃ | F | O | 1 |

-continued

| | | | | | |
|---|---|---|---|---|---|
| 603 | CH₃, C₃H₇-iso | CH₂SCH₃ | F | O | 1 |
| 604 | CH₃, C₃H₇-iso | CH₂CN | F | O | 1 |
| 605 | CH₃, C₃H₇-iso | CH₂COCH₃ | H | O | 1 |
| 606 | CH₃, C₃H₇-iso | CH₂COCH₃ | F | O | 1 |
| 607 | CH₃, C₃H₇-iso | CH₂-(isoxazol-3-yl) | H | O | 1 |
| 608 | CH₃, C₃H₇-iso | CH₂-(isoxazol-3-yl) | F | O | 1 |
| 609 | CH₃, C₃H₇-iso | CH₂-(pyridin-2-yl) | H | O | 1 |
| 610 | CH₃, C₃H₇-iso | CH₂-(pyridin-2-yl) | F | O | 1 |
| 611 | CH₃, C₄H₉-n | H | H | O | 1 |
| 612 | CH₃, C₄H₉-n | H | F | O | 1 |
| 613 | CH₃, C₄H₉-n | C₃H₇-n | F | O | 1 |
| 614 | CH₃, C₄H₉-n | CH₂CH=CH₂ | F | O | 1 |
| 615 | CH₃, C₄H₉-n | CH₂C≡CH | H | O | 1 |
| 616 | CH₃, C₄H₉-n | CH₂C≡CH | F | O | 1 |
| 617 | CH₃, C₄H₉-n | CH₂OCH₃ | F | O | 1 |
| 618 | CH₃, C₄H₉-n | CH₂SCH₃ | F | O | 1 |
| 619 | CH₃, C₄H₉-n | CH₃CN | F | O | 1 |
| 620 | CH₃, C₄H₉-n | CH₂-(isoxazol-3-yl) | H | O | 1 |
| 621 | CH₃, C₄H₉-n | CH₂-(isoxazol-3-yl) | F | O | 1 |
| 622 | CH₃, C₄H₉-n | CH₂-(pyridin-2-yl) | H | O | 1 |
| 623 | CH₃, C₄H₉-n | CH₂-(pyridin-2-yl) | F | O | 1 |
| 624 | CH₃, C₄H₉-iso | H | H | O | 1 |
| 625 | CH₃, C₄H₉-iso | H | F | O | 1 |
| 626 | CH₃, C₄H₉-iso | C₃H₇-n | F | O | 1 |
| 627 | CH₃, C₄H₉-iso | CH₂CH=CH₂ | F | O | 1 |
| 628 | CH₃, C₄H₉-iso | CH₂C≡CH | H | O | 1 |
| 629 | CH₃, C₄H₉-iso | CH₂C≡CH | F | O | 1 |
| 630 | CH₃, C₄H₉-iso | CH₂OCH₃ | F | O | 1 |
| 631 | CH₃, C₄H₉-iso | CH₂SCH₃ | F | O | 1 |
| 632 | CH₃, C₄H₉-iso | CH₂CN | F | O | 1 |
| 633 | CH₃, C₄H₉-iso | CH₂COCH₃ | H | O | 1 |
| 634 | CH₃, C₄H₉-iso | CH₂COCH₃ | F | O | 1 |
| 635 | CH₃, C₄H₉-iso | CH₂-(isoxazol-3-yl) | H | O | 1 |

| | | | | | | |
|---|---|---|---|---|---|---|
| 636 | CH₃, C₄H₉-iso | 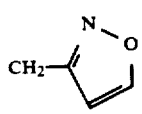 | | F | O | 1 |
| 637 | CH₃, C₄H₉-iso | 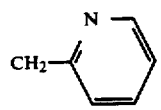 | | H | O | 1 |
| 638 | CH₃, C₄H₉-iso | 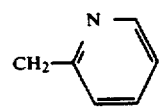 | | F | O | 1 |
| 639 | CH₃, C₄H₉-sec | H | | H | O | 1 |
| 640 | CH₃, C₄H₉-sec | H | | F | O | 1 |
| 641 | CH₃, C₄H₉-sec | C₃H₇-n | | F | O | 1 |
| 642 | CH₃, C₄H₉-sec | CH₂CH=CH₂ | | F | O | 1 |
| 643 | CH₃, C₄H₉-sec | CH₂C≡CH | | H | O | 1 |
| 644 | CH₃, C₄H₉-sec | CH₂C≡CH | | F | O | 1 |
| 645 | CH₃, C₄H₉-sec | CH₂OCH₃ | | F | O | 1 |
| 646 | CH₃, C₄H₉-sec | CH₂SCH₃ | | F | O | 1 |
| 647 | CH₃, C₄H₉-sec | CH₂CN | | F | O | 1 |
| 648 | CH₃, C₄H₉-sec | 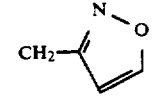 | | H | O | 1 |
| 649 | CH₃, C₄H₉-sec | 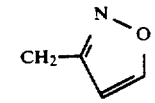 | | F | O | 1 |
| 650 | CH₃, C₄H₉-sec | 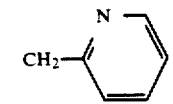 | | H | O | 1 |
| 651 | CH₃, C₄H₉-sec | 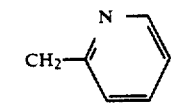 | | F | O | 1 |
| 652 | CH₃, C₄H₉-tert | H | | H | O | 1 |
| 653 | CH₃, C₄H₉-tert | H | | F | O | 1 |
| 654 | CH₃, C₄H₉-tert | C₃H₇-n | | F | O | 1 |
| 655 | CH₃, C₄H₉-tert | CH₂CH=CH₂ | | F | O | 1 |
| 656 | CH₃, C₄H₉-tert | CH₂C≡CH | | H | O | 1 |
| 657 | CH₃, C₄H₉-tert | CH₂C≡CH | | F | O | 1 |
| 658 | CH₃, C₄H₉-tert | CH₂OCH₃ | | F | O | 1 |
| 659 | CH₃, C₄H₉-tert | CH₂SCH₃ | | F | O | 1 |
| 660 | CH₃, C₄H₉-tert | CH₂CN | | F | O | 1 |
| 661 | CH₃, C₄H₉-tert | CH₂COCH₃ | | H | O | 1 |
| 662 | CH₃, C₄H₉-tert | CH₂COCH₃ | | F | O | 1 |
| 663 | CH₃, C₄H₉-tert | 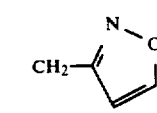 | | H | O | 1 |
| 664 | CH₃, C₄H₉-tert | 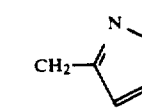 | | F | O | 1 |
| 665 | CH₃, C₄H₉-tert | 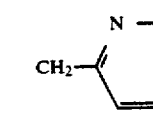 | | H | O | 1 |

| | | | | | |
|---|---|---|---|---|---|
| 666 | CH₃, C₄H₉-tert | 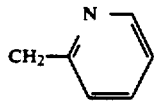 | F | O | 1 |
| 667 | C₂H₅, C₂H₅ | H | H | O | 1 |
| 668 | C₂H₅, C₂H₅ | H | F | O | 1 |
| 669 | C₂H₅, C₂H₅ | C₃H₇-n | F | O | 1 |
| 670 | C₂H₅, C₂H₅ | CH₂CH=CH₂ | F | O | 1 |
| 671 | C₂H₅, C₂H₅ | CH₂C≡CH | H | O | 1 |
| 672 | C₂H₅, C₂H₅ | CH₂C≡CH | F | O | 1 |
| 673 | C₂H₅, C₂H₅ | CH₂OCH₃ | F | O | 1 |
| 674 | C₂H₅, C₂H₅ | CH₂SCH₃ | F | O | 1 |
| 675 | C₂H₅, C₂H₅ | CH₂CN | F | O | 1 |
| 676 | C₂H₅, C₂H₅ | 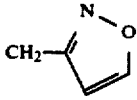 | H | O | 1 |
| 677 | C₂H₅, C₂H₅ | 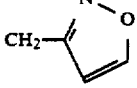 | F | O | 1 |
| 678 | C₂H₅, C₂H₅ | 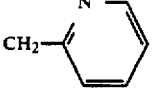 | H | O | 1 |
| 679 | C₂H₅, C₂H₅ | 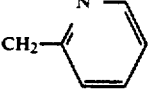 | F | O | 1 |
| 680 | C₂H₅, C₃H₇-n | H | H | O | 1 |
| 681 | C₂H₅, C₃H₇-n | H | F | O | 1 |
| 682 | C₂H₅, C₃H₇-n | C₃H₇-n | F | O | 1 |
| 683 | C₂H₅, C₃H₇-n | CH₂CH=CH₂ | F | O | 1 |
| 684 | C₂H₅, C₃H₇-n | CH₂C≡CH | H | O | 1 |
| 685 | C₂H₅, C₃H₇-n | CH₂C≡CH | F | O | 1 |
| 686 | C₂H₅, C₃H₇-n | CH₂OCH₃ | F | O | 1 |
| 687 | C₂H₅, C₃H₇-n | CH₂SCH₃ | F | O | 1 |
| 688 | C₂H₅, C₃H₇-n | CH₂CN | F | O | 1 |
| 689 | C₂H₅, C₃H₇-n | CH₂COCH₃ | H | O | 1 |
| 690 | C₂H₅, C₃H₇-n | CH₂COCH₃ | F | O | 1 |
| 691 | C₂H₅, C₃H₇-n | 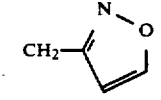 | H | O | 1 |
| 692 | C₂H₅, C₃H₇-n | 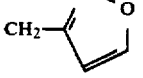 | F | O | 1 |
| 693 | C₂H₅, C₃H₇-n | 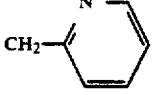 | H | O | 1 |
| 694 | C₂H₅, C₃H₇-n | 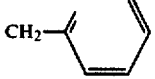 | F | O | 1 |
| 695 | C₂H₅, C₃H₇-iso | H | H | O | 1 |
| 696 | C₂H₅, C₃H₇-iso | H | F | O | 1 |
| 697 | C₂H₅, C₃H₇-iso | C₃H₇-n | F | O | 1 |
| 698 | C₂H₅, C₃H₇-iso | CH₂CH=CH₂ | F | O | 1 |
| 699 | C₂H₅, C₃H₇-iso | CH₂C≡CH | H | O | 1 |
| 700 | C₂H₅, C₃H₇-iso | CH₂C≡CH | F | O | 1 |
| 701 | C₂H₅, C₃H₇-iso | CH₂OCH₃ | F | O | 1 |

-continued

| | | | | | |
|---|---|---|---|---|---|
| 702 | C₂H₅, C₃H₇-iso | CH₂SCH₃ | F | O | 1 |
| 703 | C₂H₅, C₃H₇-iso | CH₂CN | F | O | 1 |
| 704 | C₂H₅, C₃H₇-iso | CH₂-(isoxazol-3-yl) | H | O | 1 |
| 705 | C₂H₅, C₃H₇-iso | CH₂-(isoxazol-3-yl) | F | O | 1 |
| 706 | C₂H₅, C₃H₇-iso | CH₂-(pyridin-2-yl) | H | O | 1 |
| 707 | C₂H₅, C₃H₇-iso | CH₂-(pyridin-2-yl) | F | O | 1 |
| 708 | C₂H₅, C₄H₉-n | H | H | O | 1 |
| 709 | C₂H₅, C₄H₉-n | H | F | O | 1 |
| 710 | C₂H₅, C₄H₉-n | C₃H₇-n | F | O | 1 |
| 711 | C₂H₅, C₄H₉-n | CH₂CH=CH₂ | F | O | 1 |
| 712 | C₂H₅, C₄H₉-n | CH₂C≡CH | H | O | 1 |
| 713 | C₂H₅, C₄H₉-n | CH₂C≡CH | F | O | 1 |
| 714 | C₂H₅, C₄H₉-n | CH₂OCH₃ | F | O | 1 |
| 715 | C₂H₅, C₄H₉-n | CH₂SCH₃ | F | O | 1 |
| 716 | C₂H₅, C₄H₉-n | CH₂CN | F | O | 1 |
| 717 | C₂H₅, C₄H₉-n | CH₂COCH₃ | H | O | 1 |
| 718 | C₂H₅, C₄H₉-n | CH₂COCH₃ | F | O | 1 |
| 719 | C₂H₅, C₄H₉-n | CH₂-(isoxazol-3-yl) | H | O | 1 |
| 720 | C₂H₅, C₄H₉-n | CH₂-(isoxazol-3-yl) | F | O | 1 |
| 721 | C₂H₅, C₄H₉-n | CH₂-(pyridin-2-yl) | H | O | 1 |
| 722 | C₂H₅, C₄H₉-n | CH₂-(pyridin-2-yl) | F | O | 1 |
| 723 | C₂H₅, C₄H₉-iso | H | H | O | 1 |
| 724 | C₂H₅, C₄H₉-iso | H | F | O | 1 |
| 725 | C₂H₅, C₄H₉-iso | C₃H₇-n | F | O | 1 |
| 726 | C₂H₅, C₄H₉-iso | CH₂CH=CH₂ | F | O | 1 |
| 727 | C₂H₅, C₄H₉-iso | CH₂C≡CH | H | O | 1 |
| 728 | C₂H₅, C₄H₉-iso | CH₂C≡CH | F | O | 1 |
| 729 | C₂H₅, C₄H₉-iso | CH₂OCH₃ | F | O | 1 |
| 730 | C₂H₅, C₄H₉-iso | CH₂SCH₃ | F | O | 1 |
| 731 | C₂H₅, C₄H₉-iso | CH₂CN | F | O | 1 |
| 732 | C₂H₅, C₄H₉-iso | CH₂-(isoxazol-3-yl) | H | O | 1 |

-continued

| | | | | | | |
|---|---|---|---|---|---|---|
| 733 | C₂H₅, C₄H₉-iso |  | | F | O | 1 |
| 734 | C₂H₅, C₄H₉-iso |  | | H | O | 1 |
| 735 | C₂H₅, C₄H₉-iso |  | | F | O | 1 |
| 736 | C₂H₅, C₄H₉-sec | H | | H | O | 1 |
| 737 | C₂H₅, C₄H₉-sec | H | | F | O | 1 |
| 738 | C₂H₅, C₄H₉-sec | C₃H₇-n | | F | O | 1 |
| 739 | C₂H₅, C₄H₉-sec | CH₂CH=CH₂ | | F | O | 1 |
| 740 | C₂H₅, C₄H₉-sec | CH₂C≡CH | | H | O | 1 |
| 741 | C₂H₅, C₄H₉-sec | CH₂≡CH | | F | O | 1 |
| 742 | C₂H₅, C₄H₉-sec | CH₂OCH₃ | | F | O | 1 |
| 743 | C₂H₅, C₄H₉-sec | CH₂SCH₃ | | F | O | 1 |
| 744 | C₂H₅, C₄H₉-sec | CH₂CN | | F | O | 1 |
| 745 | C₂H₅, C₄H₉-sec | CH₂COCH₃ | | H | O | 1 |
| 746 | C₂H₅, C₄H₉-sec | CH₂COCH₃ | | F | O | 1 |
| 747 | C₂H₅, C₄H₉-sec |  | | H | O | 1 |
| 748 | C₂H₅, C₄H₉-sec |  | | F | O | 1 |
| 749 | C₂H₅, C₄H₉-sec |  | | H | O | 1 |
| 750 | C₂H₅, C₄H₉-sec |  | | F | O | 1 |
| 751 | C₂H₅, C₄H₉-tert | H | | H | O | 1 |
| 752 | C₂H₅, C₄H₉-tert | H | | F | O | 1 |
| 753 | C₂H₅, C₄H₉-tert | C₃H₇-n | | F | O | 1 |
| 754 | C₂H₅, C₄H₉-tert | CH₂CH=CH₂ | | F | O | 1 |
| 755 | C₂H₅, C₄H₉-tert | CH₂C≡CH | | H | O | 1 |
| 756 | C₂H₅, C₄H₉-tert | CH₂C≡CH | | F | O | 1 |
| 757 | C₂H₅, C₄H₉-tert | CH₂OCH₃ | | F | O | 1 |
| 758 | C₂H₅, C₄H₉-tert | CH₂SCH₃ | | F | O | 1 |
| 759 | C₂H₅, C₄H₉-tert | CH₂CN | | F | O | 1 |
| 760 | C₂H₅, C₄H₉-tert |  | | H | O | 1 |
| 761 | C₂H₅, C₄H₉-tert |  | | F | O | 1 |

-continued

| | | | | | |
|---|---|---|---|---|---|
| 762 | C$_2$H$_5$, C$_4$H$_9$-tert | 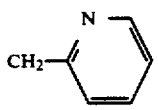 | H | O | 1 |
| 763 | C$_2$H$_5$, C$_4$H$_9$-tert | 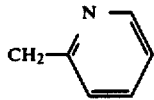 | F | O | 1 |
| 764 | C$_3$H$_7$-n, C$_3$H$_7$-n | H | H | O | 1 |
| 765 | C$_3$H$_7$-n, C$_3$H$_7$-n | H | F | O | 1 |
| 766 | C$_3$H$_7$-n, C$_3$H$_7$-n | C$_3$H$_7$-n | F | O | 1 |
| 767 | C$_3$H$_7$-n, C$_3$H$_7$-n | CH$_2$=CH$_2$ | F | O | 1 |
| 768 | C$_3$H$_7$-n, C$_3$H$_7$-n | CH$_2$C≡CH | H | O | 1 |
| 769 | C$_3$H$_7$-n, C$_3$H$_7$-n | CH$_2$C≡CH | F | O | 1 |
| 770 | C$_3$H$_7$-n, C$_3$H$_7$-n | CH$_2$OCH$_3$ | F | O | 1 |
| 771 | C$_3$H$_7$-n, C$_3$H$_7$-n | CH$_2$SCH$_3$ | F | O | 1 |
| 772 | C$_3$H$_7$-n, C$_3$H$_7$-n | CH$_2$CN | F | O | 1 |
| 773 | C$_3$H$_7$-n, C$_3$H$_7$-n | CH$_2$COCH$_3$ | H | O | 1 |
| 774 | C$_3$H$_7$-n, C$_3$H$_7$-n | CH$_2$COCH$_3$ | F | O | 1 |
| 775 | C$_3$H$_7$-n, C$_3$H$_7$-n | 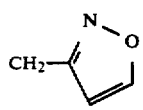 | H | O | 1 |
| 776 | C$_3$H$_7$-n, C$_3$H$_7$-n | 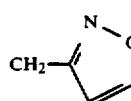 | F | O | 1 |
| 777 | C$_3$H$_7$-n, C$_3$H$_7$-n | 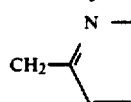 | H | O | 1 |
| 778 | C$_3$H$_7$-n, C$_3$H$_7$-n | 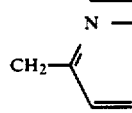 | F | O | 1 |
| 779 | C$_3$H$_7$-n, C$_4$H$_9$-n | CH$_2$C≡CH | F | O | 1 |
| 780 | C$_3$H$_7$-n, C$_4$H$_9$-iso | CH$_2$C≡CH | F | O | 1 |
| 781 | C$_3$H$_7$-n, C$_4$H$_9$-iso | CH$_2$C≡CH | F | O | 1 |
| 782 | C$_3$H$_7$-n, C$_4$H$_9$-iso | CH$_2$COCH$_3$ | F | O | 1 |
| 783 | C$_3$H$_7$-n, C$_4$H$_9$-sec | CH$_2$=CH | F | O | 1 |
| 784 | C$_3$H$_7$-n, C$_4$H$_9$-sec | CH$_2$COCH$_3$ | F | O | 1 |
| 785 | C$_3$H$_7$-n, C$_4$H$_9$-tert | CH$_2$C≡CH | F | O | 1 |
| 786 | C$_3$H$_7$-n, C$_4$H$_9$-tert | CH$_2$COCH$_3$ | F | O | 1 |
| 787 | C$_4$H$_9$-n, C$_4$H$_9$-n | CH$_2$C≡CH | F | O | 1 |
| 788 | C$_4$H$_9$-n, C$_4$H$_9$-n | CH$_2$COCH$_3$ | F | O | 1 |
| 789 | C$_4$H$_9$-n, C$_4$H$_9$-n | CH$_2$C≡CH | F | O | 1 |
| 790 | C$_4$H$_9$-n, C$_4$H$_9$-iso | CH$_2$C≡CH | F | O | 1 |
| 791 | C$_4$H$_9$-n, C$_4$H$_9$-sec | CH$_2$C≡CH | F | O | 1 |
| 792 | C$_4$H$_9$-n, C$_4$H$_9$-sec | CH$_2$COCH$_3$ | F | O | 1 |
| 793 | —(CH$_2$)$_4$— | H | F | O | 1 mp.230–234°C. |
| 794 | —(CH$_2$)$_4$— | CH$_3$ | F | O | 1 |
| 795 | —(CH$_2$)$_4$— | C$_2$H$_5$ | F | O | 1 |
| 796 | —(CH$_2$)$_4$— | C$_3$H$_7$-n | F | O | 1 mp. 125–129°C. |
| 797 | —(CH$_2$)$_4$— | C$_4$H$_9$-n | F | O | 1 |
| 798 | —(CH$_2$)$_4$— | C$_4$H$_9$-iso | F | O | 1 |
| 799 | —(CH$_2$)$_4$— | C$_4$H$_9$-sec | F | O | 1 |
| 800 | —(CH$_2$)$_4$— | CH$_2$CH$_2$F | F | O | 1 |
| 801 | —(CH$_2$)$_4$— | CH$_2$CH$_2$CH$_2$CL | F | O | 1 |
| 802 | —(CH$_2$)$_4$— | CH$_2$—◁ | F | O | 1 Oily |
| 803 | —(CH$_2$)$_4$— | CH$_2$CH$_2$=CH$_2$ | F | O | 1 |
| 804 | —(CH$_2$)$_4$— | CH$_2$CH$_2$CH$_2$=CH$_2$ | F | O | 1 |
| 805 | —(CH$_2$)$_4$— | CH$_2$C(Cl)=CH$_2$ | F | O | 1 Oily |
| 806 | —(CH$_2$)$_4$— | CH$_2$CH=CHCL | F | O | 1 |
| 807 | —(CH$_2$)$_4$— | CH$_2$C(Cl)=CHCl | F | O | 1 |

| | | | | | | |
|---|---|---|---|---|---|---|
| 808 | —(CH$_2$)$_4$— | CH$_2$C(Cl)=CCl$_2$ | F | O | 1 | |
| 809 | —(CH$_2$)$_4$— | CH$_2$C≡CH | H | O | 1 | |
| 810 | —(CH$_2$)$_4$— | CH$_2$C≡CH | F | O | 1 | mp. 122—132°C. |
| 811 | —(CH$_2$)$_4$— | CH(CH$_3$)C≡CH | F | O | 1 | |
| 812 | —(CH$_2$)$_4$— | CH$_2$OCH$_3$ | F | O | 1 | |
| 813 | —(CH$_2$)$_4$— | CH$_2$OC$_2$H$_5$ | F | O | 1 | |
| 814 | —(CH$_2$)$_4$— | CH$_2$CH$_2$OC$_2$H$_5$ | F | O | 1 | |
| 815 | —(CH$_2$)$_4$— | CH$_2$SCH$_3$ | F | O | 1 | |
| 816 | —(CH$_2$)$_4$— | CH$_2$SC$_2$H$_5$ | F | O | 1 | |
| 817 | —(CH$_2$)$_4$— | CH$_2$CH$_2$SC$_2$H$_5$ | F | O | 1 | |
| 818 | —(CH$_2$)$_4$— | CH$_2$S(O)CH$_3$ | F | O | 1 | |
| 819 | —(CH$_2$)$_4$— | CH$_2$S(O)$_2$CH$_3$ | F | O | 1 | |
| 820 | —(CH$_2$)$_4$— | CH$_2$S—C$_6$H$_5$ | F | O | 1 | |
| 821 | —(CH$_2$)$_4$— | CH$_2$S—C$_6$H$_4$-4-Cl | F | O | 1 | |
| 822 | —(CH$_2$)$_4$— | CH$_2$S(O)—C$_6$H$_5$ | F | O | 1 | |
| 823 | —(CH$_2$)$_4$— | CH$_2$S(O)$_2$—C$_6$H$_5$ | F | O | 1 | |
| 824 | —(CH$_2$)$_4$— | CH$_2$CN | F | O | 1 | mp. 199—202° C. |
| 825 | —(CH$_2$)$_4$— | CH(CH$_3$)—CN | F | O | 1 | |
| 826 | —(CH$_2$)$_4$— | CH$_2$CONH$_2$ | F | O | 1 | |
| 827 | —(CH$_2$)$_4$— | CH$_2$CSNH$_2$ | F | O | 1 | |
| 828 | —(CH$_2$)$_4$— | CH$_2$Si(CH$_3$)$_3$ | F | O | 1 | |
| 829 | —(CH$_2$)$_4$— | CH$_2$—C$_6$H$_5$ | F | O | 1 | |
| 830 | —(CH$_2$)$_4$— | CH$_2$—C$_6$H$_4$-4-CH$_3$ | F | O | 1 | |
| 831 | —(CH$_2$)$_4$— | CH$_2$—C$_6$H$_4$-4-OCH$_3$ | F | O | 1 | |
| 832 | —(CH$_2$)$_4$— | CH$_2$—C$_6$H$_4$-4-Cl | F | O | 1 | |
| 833 | —(CH$_2$)$_4$— | CH$_2$—C$_6$H$_4$-2-F | F | O | 1 | |
| 834 | —(CH$_2$)$_4$— | CH$_2$COCH$_3$ | H | O | 1 | |
| 835 | —(CH$_2$)$_4$— | CH$_2$COCH$_3$ | F | O | 1 | Oily |
| 836 | —(CH$_2$)$_4$— | CH$_2$COC$_2$H$_5$ | F | O | 1 | |
| 837 | —(CH$_2$)$_4$— | CH(CH$_3$)COC$_2$H$_5$ | F | O | 1 | |

-continued

| | | | | | | |
|---|---|---|---|---|---|---|
| 838 | —(CH₂)₄— | $\underset{\text{CHCOC}_3\text{H}_7}{\overset{\text{C}_2\text{H}_5}{|}}$ | F | O | 1 | |
| 839 | —(CH₂)₄— | CH₂CO—C₆H₅ (phenyl) | F | O | 1 | |
| 840 | —(CH₂)₄— | CH₂CO—C₆H₄—CH₃ | F | O | 1 | |
| 841 | —(CH₂)₄— | CH₂CO—C₆H₄—Cl | F | O | 1 | |
| 842 | —(CH₂)₄— | CH₂C(=N—OH)—CH₃ | F | O | 1 | mp.185–188° C. |
| 843 | —(CH₂)₄— | CH₂C(=N—OH)—C₆H₅ | F | O | 1 | |
| 844 | —(CH₂)₄— | CH₂C(=N—OCH₃)—CH₃ | F | O | 1 | |
| 845 | —(CH₂)₄— | CH₂C(=N—OCH₃)—C₆H₅ | F | O | 1 | |
| 846 | —(CH₂)₄— | CH₂C(=N—OC₂H₅)—CH₃ | F | O | 1 | |
| 847 | —(CH₂)₄— | CH₂C(=N—OCH₂CH=CH₂)—CH₃ | F | O | 1 | |
| 848 | —(CH₂)₄— | CH₂C(=N—OCH₂C≡CH)—CH₃ | F | O | 1 | |
| 849 | —(CH₄)₄— | CH₂C(=N—OCH₂—C₆H₅)—CH₃ | F | O | 1 | |
| 850 | —(CH₂)₄— | CH₂C(=N—OCOCH₃)—CH₃ | F | O | 1 | |
| 851 | —(CH₂)₄— | CH₂C(=N—OSO₂CH₃)—CH₃ | F | O | 1 | |
| 852 | —(CH₂)₄— | $\underset{\text{CH—C—C}_2\text{H}_5}{\overset{\text{CH}_3 \ \ \text{N—OH}}{|\ \ \ \ \ ||}}$ | F | O | 1 | |
| 853 | —(CH₂)₄— | $\underset{\text{CH—C—C}_3\text{H}_7}{\overset{\text{C}_2\text{H}_5 \ \ \text{N—OH}}{|\ \ \ \ \ ||}}$ | F | O | 1 | |
| 854 | —(CH₂)₄— | CH₂C(=NN(CH₃)₂)—CH₃ | F | O | 1 | |
| 855 | —(CH₂)₄— | CH₂C(=NN(C₂H₅)₂)—C₂H₅ | F | O | 1 | |
| 856 | —(CH₂)₄— | CH₂C(CH₃)=NN(COCH₃)(CH₃) | F | O | 1 | |
| 857 | —(CH₂)₄— | CH₂CH₂N(CH₃)₂ | F | O | 1 | |
| 858 | —(CH₂)₄— | CH₂CH₂CH₂N(CH₃)₂ | F | O | 1 | |
| 859 | —(CH₂)₄— | 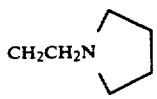 | | | | |

-continued

| No. | | | | | | |
|---|---|---|---|---|---|---|
| 860 | —(CH$_2$)$_4$— | CH$_2$CH$_2$N-piperidine | F | O | 1 | |
| 861 | —(CH$_2$)$_4$— | CH$_2$CH$_2$N-morpholine | F | O | 1 | |
| 862 | —(CH$_2$)$_4$— | CH$_2$CH$_2$N-(N'-methylpiperazine) | F | O | 1 | |
| 863 | —(CH$_2$)$_4$— | CH$_2$CH$_2$N(COCH$_3$)—C$_3$H$_7$-iso | F | O | 1 | |
| 864 | —(CH$_2$)$_4$— | CH$_2$CH$_2$N(SO$_2$CH$_3$)—CH$_3$ | F | O | 1 | |
| 865 | —(CH$_2$)$_4$— | CH$_2$COOC$_2$H$_5$ | F | O | 1 | mp. 144—146.° C. |
| 866 | —(CH$_2$)$_4$— | CH$_2$COO-cyclopentyl(H) | F | O | 1 | |
| 867 | —(CH$_2$)$_4$— | CH(CH$_3$)COOC$_2$H$_5$ | F | O | 1 | |
| 868 | —(CH$_2$)$_4$— | CH$_2$COOH$_2$CF$_3$ | F | O | 1 | |
| 869 | —(CH$_2$)$_4$— | CH$_2$CONHC$_3$H$_7$-iso | F | O | 1 | |
| 870 | —(CH$_2$)$_4$— | CH$_2$CON(CH$_3$)$_2$ | F | O | 1 | |
| 871 | —(CH$_2$)$_4$— | CH$_2$CON(C$_3$H$_7$-n)$_2$ | F | O | 1 | |
| 872 | —(CH$_2$)$_4$— | CH$_2$CON-piperidine | F | O | 1 | |
| 873 | —(CH$_2$)$_4$— | CH$_2$CON(CH$_3$)—C$_6$H$_5$ | F | O | 1 | |
| 874 | —(CH$_2$)$_4$— | CH$_2$CON(C$_3$H$_7$-iso)—C$_6$H$_5$ | F | O | 1 | |
| 875 | —(CH$_2$)$_4$— | CH$_2$CON(CH$_3$)—(2-CH$_3$-C$_6$H$_4$) | F | O | 1 | |
| 876 | —(CH$_2$)$_4$— | CH$_2$CON(CH$_3$)—(3-Cl-C$_6$H$_4$) | F | O | 1 | |
| 877 | —(CH$_2$)$_4$— | CH$_2$COOCH$_2$Si(CH$_3$)$_3$ | F | O | 1 | |
| 878 | —(CH$_2$)$_4$— | CH$_2$-1,2,4-triazol-1-yl | F | O | 1 | |
| 879 | —(CH$_2$)$_4$— | CH$_2$-isoxazol-3-yl | H | O | 1 | |
| 880 | —(CH$_2$)$_4$— | CH$_2$-isoxazol-3-yl | F | O | 1 | |

-continued

| # | R | R' | X | Y | n | mp |
|---|---|---|---|---|---|---|
| 881 | —(CH$_2$)$_4$— | CH$_2$-(thiazole) | F | O | 1 | |
| 882 | —(CH$_2$)$_4$— | CH$_2$-(5-methyl-1,2,4-oxadiazol-3-yl) | F | O | 1 | |
| 883 | —(CH$_2$)$_4$— | CH$_2$-(4-methyl-furazan-3-yl) | F | O | 1 | |
| 884 | —(CH$_2$)$_4$— | CH$_2$-(4-methyl-1,2,5-thiadiazol-3-yl) | F | O | 1 | |
| 885 | —(CH$_2$)$_4$— | CH$_2$-(pyridazin-3-yl) | H | O | 1 | mp. 114–116° C. |
| 886 | —(CH$_2$)$_4$— | CH$_2$-(pyridin-2-yl) | F | O | 1 | |
| 887 | —(CH$_2$)$_4$— | CH$_2$-(pyrazin-2-yl) | F | O | 1 | |
| 888 | —(CH$_2$)$_4$— | CH$_2$CN | CL | O | 1 | mp. 163–168° C. |
| 889 | —CH$_2$CH=CHCH$_2$— | H | F | S | 0 | |
| 890 | —CH$_2$CH=CHCH$_2$— | CH$_3$ | F | S | 0 | |
| 891 | —CH$_2$CH=CHCH$_2$— | C$_2$H$_5$ | F | S | 0 | |
| 892 | —CH$_2$CH=CHCH$_2$— | C$_3$H$_7$-n | F | S | 0 | |
| 893 | —CH$_2$CH=CHCH$_2$— | CH$_2$-cyclopropyl | F | S | 0 | |
| 894 | —CH$_2$CH=CHCH$_2$— | CH$_2$OCH$_3$ | F | S | 0 | |
| 895 | —CH$_2$CH=CHCH$_2$— | CH$_2$SCH$_3$ | F | S | 0 | |
| 896 | —CH$_2$CH=CHCH$_2$— | CH$_2$CH=CH$_2$ | F | S | 0 | |
| 897 | —CH$_2$CH=CHCH$_2$— | CH$_2$C≡CH | F | S | 0 | mp. 132–135° C. |
| 898 | —CH$_2$CH=CHCH$_2$— | CH$_2$CN | F | S | 0 | |
| 899 | —CH$_2$CH=CHCH$_2$— | CH$_2$-(isoxazol-4-yl) | F | S | 0 | |
| 900 | —CH$_2$CH=CHCH$_2$— | CH$_2$-(5-methyl-1,2,4-oxadiazol-3-yl) | F | S | 0 | |
| 901 | —CH$_2$CH=CHCH$_2$— | CH$_2$-(pyridazin-3-yl) | F | S | 0 | |
| 902 | —CH$_2$CH=CHCH$_2$— | H | F | O | 1 | |
| 903 | —CH$_2$CH=CHCH$_2$— | CH$_3$ | F | O | 1 | |
| 904 | —CH$_2$CH=CHCH$_2$— | C$_2$H$_5$ | F | O | 1 | |
| 905 | —CH$_2$CH=CHCH$_2$— | C$_3$H$_7$-n | F | O | 1 | |
| 906 | —CH$_2$CH=CHCH$_2$— | CH$_2$-cyclopropyl | F | O | 1 | |
| 907 | —CH$_2$CH=CHCH$_2$— | CH$_2$OCH$_3$ | F | O | 1 | |
| 908 | —CH$_2$CH=CHCH$_2$— | CH$_2$SCH$_3$ | F | O | 1 | |
| 909 | —CH$_2$CH=CHCH$_2$— | CH$_2$CH=CH$_2$ | F | O | 1 | |
| 910 | —CH$_2$CH=CHCH$_2$— | CH$_2$C≡CH | | | | |
| 911 | —CH$_2$CH=CHCH$_2$— | CH$_2$CN | F | O | 1 | |
| 912 | —CH$_2$CH=CHCH$_2$— | CH$_2$-(isoxazol-4-yl) | F | O | 1 | |

| 913 | —CH₂CH=CHCH₂— | 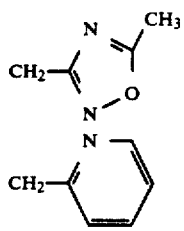 | F | O | 1 |
| 914 | —CH₂CH=CHCH₂— | 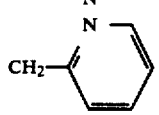 | F | O | 1 |

BIOLOGICAL EXAMPLE

EXAMPLE 4

Submerged application test against lowland weeds under flooding condition

Formulation of Active Compounds

Carrier: 5 parts by weight of acetone

Emulsifier: 1 part by weight of benzyloxy polyglycol ether.

To produce a suitable preparation of active compound, 1 part by weight of active compound was mixed with the stated amount of carrier and with the stated amount of emulsifier, and the resulting emulsifiable concentrate was then diluted with water to the desired concentrations.

Test Procedures

Each of several pots, having a size of 25×20×9 cm and an area of 1/2,000 are, was filled with soil taken out from a paddy field. Young paddy-rice plants (Nihonbare Variety) of the 2.5-leaf stage, with a height of 15 cm, were transplanted into these pots. Each pot has two zones, with the number of the plants grown in each zone being three. Then, seeds of the following weeds were sown in the soil, which was kept under wet conditions:

barnyard grass (*Echinochloa crus-galli*); umbrella plant (*Cyperus diformis*); monochoria (*Monochoria vaginalis*); and annual broad-leaved weeds such as false pimpernel (*Lindernia pyxidaria*), toothcup (*Rotala indica*), American waterwort (*Elatine triandra*), Red stem (*Ammannia multiflora*), and dopatrium (Dopatrium).

After 2 days, water was introduced to a depth of 2–3 cm over the soil surface in each pot. Five days after the transplantion of the rice plants, the emulsion of the active compound, which had been prepared in the manner mentioned above, was applied to the pots in a predetermined amount by means of a pipette. After that, the water depth was kept at about 3 cm.

Four weeks after the application of the active compound, the degree of damage to the weeds and the degree of phytotoxicity on the paddy-rice plants were determined, and recorded according to the following assessment scale rated from 0 to 5.

| Rating | Herbicidal effect of active compound on weed in %* |
|---|---|
| 5 | 95% or more (fatal effect) |
| 4 | at least 80% and less than 95% |
| 3 | at least 50% and less than 80% |
| 2 | at lease 30% and less than 50% |
| 1 | at least 10% and less than 30% |
| 0 | less than 10% (no herbicidal effect) |

| Rating | Phytotoxic effect of active compound on crops in %* |
|---|---|
| 5 | at least 90% (fatal phytotoxicity) |
| 4 | at least 50% and less than 90% |
| 3 | at least 30% and less than 50% |
| 2 | at least 10% and less than 30% |
| 1 | more than 0% and less than 10% |
| 0 | 0% (no phytotoxicity) |

*These values (%) are those obtained by comparing the test data in the treated section with the test data in the control (untreated) section.

The test results are shown in Table 2.

TABLE 2

| Active compound No. | Amount of active compound (kg/ha) | Herbicidal effect on weeds | | | | Phytotoxic effect on rice plants |
|---|---|---|---|---|---|---|
| | | Barnyard grass | Umbrella plant | Monochoria | Annual broad-leaved grass | |
| 18 | 0.25 | 5 | 5 | 5 | 5 | 1 |
| 408 | 0.25 | 4 | 5 | 4 | 5 | 0 |
| 490 | 0.25 | 4 | 5 | 5 | 5 | 0 |
| 796 | 0.25 | 5 | 5 | 4 | 5 | 0 |
| 810 | 0.25 | 5 | 5 | 5 | 5 | 1 |
| 824 | 0.25 | 4 | 5 | 5 | 5 | 0 |
| 897 | 0.25 | 3 | 5 | 5 | 5 | 0 |

EXAMPLE 5

Pre-emergence soil treatment test against upland weeds

In a greenhouse, a number of pots, each having an area of 500 cm², were charged with soil obtained from a cultivated field. Seeds of soy bean were sown into the soil in the pots. Thereafter the surface of the soil was covered with a soil layer. The soil layer contained seeds of fingergrass (Digitaria), wild blite (Amaranthus) and goosefoot (*Chenopodium album*). The thickness of the soil layer was about 1 cm.

One day after the sowing, a predetermined amount of the preparation of the active compound, which had been produced in the same manner as in Example 4, was uniformly applied to the top soil layer in each pot.

Four weeks after the application of the active compound, the degree of damage to the weeds and the degree of phytotoxicity on the crops were determined in the same manner as in Example 4. The test results are shown in Table 3.

TABLE 3

| Active compound No. | Amount of active compound (kg/ha) | Herbicidal effect on weeds | | | Phytotoxic effect on soy bean plants |
|---|---|---|---|---|---|
| | | Fingergrass | Wild blite | Goosefoot | |
| 18 | 0.5 | 4 | 5 | 5 | 0 |
| 338 | 0.5 | 3 | 5 | 5 | 0 |
| 490 | 0.5 | 4 | 5 | 5 | 0 |
| 810 | 0.5 | 4 | 5 | 5 | 0 |
| 835 | 0.5 | 4 | 5 | 5 | 0 |

EXAMPLE 6

Herbicidal test by foliage application on upland weeds

In a greenhouse, a number of pots, each having an area of 500 cm², were charged with soil obtained from a cultivated field. Seeds of wheat (*Triticum sativium Linuaeus*) were sown onto the soil in the pots. Thereafter, the surface of the soil was covered with a soil layer. The soil layer contained seeds of fingergrass (Digitaria), wild blite (Amaranthus) and goosefoot (*Chenopodium album*). The thickness of the soil layer was about 1 cm.

The wheat plants were grown for 14 days, and then the plants were uniformly sprayed with a predetermined amount of the formulation of the active compound which had been produced in the same manner as in Example 4.

Four weeks after the application of the active compound, the degree of damage to the weeds and the degree of phytotoxicity on the wheat plants were determined in the same manner as in Example 4. The test results are shown in Table 4.

TABLE 4

| Active compound No. | Amount of active compound (kg/ha) | Herbicidal effect on weeds | | | Phytotoxicity on wheat plants |
|---|---|---|---|---|---|
| | | Finger-grass | Wild blite | Goose-foot | |
| 18 | 0.25 | 4 | 5 | 5 | 1 |
| 338 | 0.25 | 5 | 5 | 5 | 1 |
| 408 | 0.25 | 3 | 5 | 5 | 0 |
| 490 | 0.25 | 4 | 5 | 5 | 0 |
| 796 | 0.25 | 4 | 5 | 5 | 0 |
| 810 | 0.25 | 5 | 5 | 5 | 1 |

It will be appreciated that the instant specification and claims are set forth by way of illustration and not limitation, and that various modifications and changes may be made without departing from the spirit and scope of the present invention.

What is claimed is:

1. A pyrrole of the formula

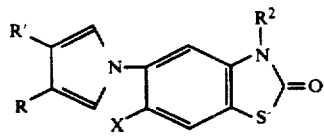

(I)

wherein $R^1$ represents $C_{1-4}$ alkyl, or one $R^1$ together with the other $R^1$ forms tetramethylene or butenylene, X represents hydrogen or halogen, $R^2$ represents hydrogen, $C_{1-5}$ alkyl, halogeno-$C_{1-5}$ alkyl, cyclopropylmethyl, $C_{3-4}$ alkenyl, halogeno-$C_{3-4}$ alkenyl, $C_{3-4}$ alkynyl, $C_{1-3}$ alkoxy-$C_{1-2}$ alkyl, $C_{1-3}$ alkylthio-$C_{1-2}$ alkyl, $C_{1-3}$ alkylsulfinyl-$C_{1-2}$ alkyl, $C_{1-3}$ alkylsulfonyl-$C_{1-2}$ alkyl, phenylthio-$C_{1-2}$ alkyl optionally substituted by halogen; phenylsulfinyl-$C_{1-2}$ alkyl, phenylsulfonyl-$C_{1-2}$ alkyl, cyano-$C_{1-2}$ alkyl, carbamoylmethyl, thiocarbamoylmethyl, tri-$C_{1-3}$ alkylsilylmethyl, phenyl-$C_{1-2}$ alkyl optionally substituted by halogen, methyl or methoxy; or $R^2$ represents

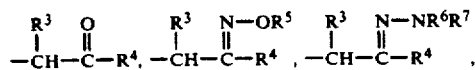

-continued

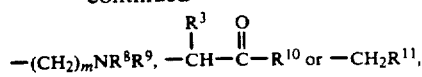

wherein m represents 2 or 3, $R^3$ represents hydrogen or $C_{1-4}$ alkyl, $R^4$ represents $C_{1-4}$ alkyl, or phenyl optionally substituted by halogen or $C_{1-4}$ alkyl, $R^5$ represents hydrogen, $C_{1-4}$ alkyl, $C_{3-4}$ alkenyl, $C_{3-4}$ alkynyl, benzyl, $C_{1-4}$-alkyl-carbonyl, or $C_{1-4}$ alkanesulfonyl, $R^6$ and $R^7$ each represent $C_{1-4}$ alkyl or $C_{1-4}$ alkylcarbonyl, $R^8$ represents $C_{1-5}$ alkyl, $R^9$ represents $C_{1-5}$ alkyl or $C_{1-4}$ alkyl-carbonyl or $R^8$ and $R^9$ together with the nitrogen atom to which they are bonded form a pyrrolidine, piperidine, N-methylpiperazine, piperazine or morpholine radical, $R^{10}$ represents $C_{1-6}$ alkoxy, $C_{3-7}$ cycloalkoxy, $C_{2-3}$ haloalkoxy, $C_{1-5}$ alkylamino, $C_{2-8}$ dialkylamino, or N-$C_{1-4}$ alkyl-N-phenylamino wherein the phenyl of the N-phenyl may be substituted by halogen and/or methyl or $R^{10}$ represents N,N-$C_{4-6}$ polymethyleneamino or tri-$C_{1-3}$ alkylsilylmethoxy, and $R^{11}$ represents a triazole, thiazole, isoxazole, oxadiazole, thiadiazole, pyridine or pyrazine radical optionally substituted by $C_{1-4}$ alkyl or $C_{1-4}$ alkoxy.

2. A compound according to claim 1, in which $R^1$ represents $C_{1-4}$ alkyl, or one $R^1$ together with the other $R^1$, forms tetramethylene or butenylene, X represents hydrogen, chlorine or fluorine, $R^2$ represents hydrogen, $C_{1-3}$ alkyl, cyclopropylmethyl, $C_3$ alkenyl optionally substituted by chlorine; propargyl, $C_{1-2}$ alkoxy-$C_{1-2}$-alkyl, $C_{1-2}$ alkylthio-$C_{1-2}$ alkyl, $C_{1-2}$ alkylsulfinyl-$C_{1-2}$ alkyl, $C_{1-2}$ alkylsulfonyl-$C_{1-2}$ alkyl, phenylthiomethyl optionally substituted by chlorine; phenylsulfinylmethyl, phenylsulfonylmethyl, cyanomethyl, carbamoylmethyl, thiocarbamoylmethyl, trimethylsilylmethyl, benzyl optionally substituted by fluorine, chlorine, methyl or methoxy, or $R^2$ represents

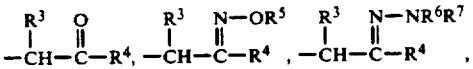

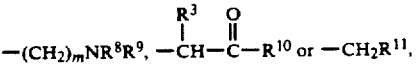

in which m represents 2 or 3, $R^3$ represents hydrogen, methyl or ethyl, $R^4$ represents methyl, ethyl, propyl or isopropyl, or phenyl which is optionally substituted by chlorine or methyl, $R^5$ represents hydrogen, methyl, ethyl, propyl, isopropyl, allyl, propargyl, benzyl, acetyl or methanesulfonyl, $R^6$ and $R^7$ represent methyl, ethyl or acetyl, $R^8$ represents $C_{1-4}$ alkyl, $R^9$ represents $C_{1-4}$ alkyl, acetyl or methanesulfonyl or $R^8$ and $R^9$ together with the adjoining nitrogen atom forms a pyrrolidine, piperidine, N-methylpiperazine, piperazine or morpholine radical, $R^{10}$ represents $C_{1-4}$ alkoxy, $C_{3-6}$ $C_{2-3}$ fluoroalkoxy, $C_{1-4}$ alkylamino, $C_{2-6}$ dialkylamino, N-$C_{1-3}$ alkyl-N-phenylamino wherein the phenyl of the N-phenyl may be substituted by chlorine and/or methyl, or $R^{10}$ represents piperidino or trimethylsilylmethoxy, and $R^{11}$ represents a triazole, thiazole, isoxazole, oxadiazole, thiadiazole, pyridine or pyrazine radical optionally be substituted by methyl, methoxy or ethoxy.

3. A compound according to claim 1, in which
$R^1$ represents methyl or one $R^1$ together with the other $R^1$ forms tetramethylene or butenylene,
X represents fluorine,
$R^2$ represents hydrogen, methyl, ethyl, n- or i-propyl, cyclopropylmethyl, allyl optionally substituted by chlorine; methoxymethyl, ethoxymethyl, methylthiomethyl, ethylthiomethyl, methylsulfinylmethyl, methylsulfonylmethyl, 2-oxopropyl, methoxycarbonylmethyl, ethoxycarbonylmethyl or —CH$_2$R$^{11}$, in which
$R^{11}$ represents a triazole, thiazole, isoxazole, oxadiazole, thiadiazole, pyridine or pyrazine radical which may optionally be substituted by methyl.

4. A compound according to claim 1, wherein such compound is 2-(6-fluoro-2-benzothiazolon-5-yl)-4,5,6,7-tetrahydroisobenzindole of the formula

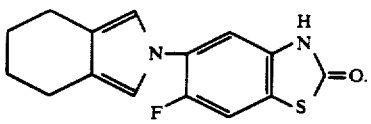

5. A compound according to claim 1, wherein such compound is 2-(6-fluoro-3-propargyl-2-benzothiazolon-5-yl)-4,5,6,7-tetrahydroisobenzindole of the formula

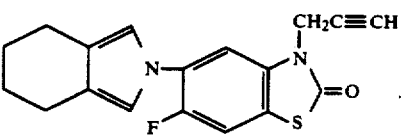

6. A herbicidal composition comprising a herbicidally effective amount of a compound according to claim 1 and a diluent.

7. A method of combatting unwanted vegetation which comprises applying thereto or to a locus from which it is desired to exclude such vegetation a herbicidally effective amount of a compound according to claim 1.

8. The method according to claim 7, wherein such compound is
2-(6-fluoro-2benzothiazolon-5-yl)-4,5,6,7-tetrahydroisobenzindole, or
2-(6-fluoro-3-propargyl-2-benzothiazolon-5-yl)-4,5,6,7-tetrahydroisobenzindole.

* * * * *

UNITED STATES PATENT AND TRADEMARK OFFICE
CERTIFICATE OF CORRECTION

PATENT NO. : 5,007,952
DATED : April 16, 1991
INVENTOR(S) : Kume et al.

It is certified that error appears in the above-identified patent and that said Letters Patent is hereby corrected as shown below:

Col. 79, line 45    Delete " 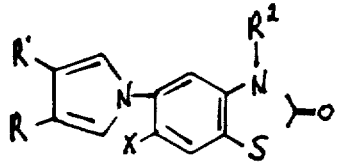 " and substitute

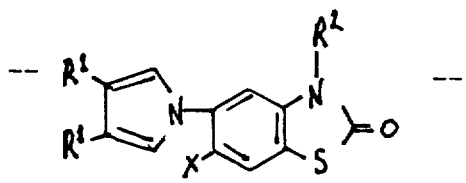

Col. 81, line 3,   After " C 3-6 " insert -- cycloalkoxy --

Signed and Sealed this

Nineteenth Day of July, 1994

Attest:

BRUCE LEHMAN

Attesting Officer        Commissioner of Patents and Trademarks